(12) United States Patent
Faivre et al.

(10) Patent No.: US 7,892,525 B2
(45) Date of Patent: Feb. 22, 2011

(54) ANTIPERSPIRANT GEL COMPOSITIONS

(75) Inventors: David Faivre, Brussels (BE); Pinky G. Purohit, Brookpark, OH (US); Krishnan Tamareselvy, Brecksville, OH (US); Duane Gerard Krzysik, Hudson, OH (US); Dorina Ghirardi, Brussels (BE); Alan Joseph Suares, University Heights, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 554 days.

(21) Appl. No.: 11/856,322

(22) Filed: Sep. 17, 2007

(65) Prior Publication Data
US 2008/0014160 A1 Jan. 17, 2008

Related U.S. Application Data

(63) Continuation-in-part of application No. 10/646,856, filed on Aug. 22, 2003, now Pat. No. 7,378,479.

(60) Provisional application No. 60/845,541, filed on Sep. 18, 2006.

(51) Int. Cl.
*A61Q 15/00* (2006.01)
(52) U.S. Cl. .............................. 424/65; 424/66; 424/68; 424/401
(58) Field of Classification Search ............... 424/65, 424/66, 68, 401
See application file for complete search history.

(56) References Cited

U.S. PATENT DOCUMENTS

| 4,384,096 A | 5/1983 | Sonnabend |
|---|---|---|
| 4,421,902 A | 12/1983 | Chang et al. |
| 4,514,552 A | 4/1985 | Shay et al. |
| 4,600,761 A | 7/1986 | Ruffner et al. |
| 4,616,074 A | 10/1986 | Ruffner |
| RE33,156 E | 1/1990 | Shay et al. |
| 5,011,978 A | 4/1991 | Barron et al. |
| 5,136,063 A | 8/1992 | O'Lenick, Jr. |
| 5,180,843 A | 1/1993 | O'Lenick, Jr. |
| 5,292,843 A | 3/1994 | Jenkins et al. |
| 5,294,692 A | 3/1994 | Barron et al. |
| 5,412,142 A | 5/1995 | Wilkerson, III et al. |
| 5,639,841 A | 6/1997 | Jenkins |
| 5,770,760 A | 6/1998 | Robinson |
| 6,140,435 A | 10/2000 | Zanotti-Russo |
| 6,391,291 B1 * | 5/2002 | Clare et al. ................ 424/65 |
| 2004/0052746 A1 | 3/2004 | Tamareselvy et al. |

FOREIGN PATENT DOCUMENTS

WO 2005087188 9/2005

OTHER PUBLICATIONS

Charles Todd and Timothy Byers, Volatile silicone fluids for cosmetics formulation, Cosmetics and Toiletries vol. 91(1), 1976, pp. 29-32.
Kenneth A. Kasprzak, Volatile Silicones, Soap/Cosmetics/Chemical Specialities, Dec. 1986, pp. 40-43.

* cited by examiner

*Primary Examiner*—Bernard Lipman
(74) *Attorney, Agent, or Firm*—Thoburn T. Dunlap

(57) ABSTRACT

The present invention relates to antiperspirant compositions comprising a cationic hydrophobically modified polymeric gelling agent and an acidic antiperspirant compound. The antiperspirant compositions are transparent, phase stable, non-whitening and non-staining to the skin and clothing following topical application. The present invention also is directed to methods of using the antiperspirant compositions.

17 Claims, 2 Drawing Sheets

ANTIPERSPIRANT GEL COMPOSITIONS

RELATED APPLICATION

This application is a continuation-in-part of U.S. application Ser. No. 10/646,856 filed on Aug. 22, 2003, and claims the benefit of U.S. Provisional application Ser. No. 60/845,541, filed on Sep. 18, 2006.

TECHNICAL FIELD OF THE INVENTION

The present invention relates to antiperspirant compositions comprising a cationic hydrophobically modified polymeric gelling agent and an acidic antiperspirant compound. The antiperspirant compositions are transparent, phase stable, non-whitening and non-staining to the skin and clothing after topical application. The present invention also is directed to methods of using the antiperspirant compositions.

BACKGROUND

Antiperspirant compositions are commonly applied to the skin at the underarms to prevent or alleviate perspiration. Such compositions take a variety of physical forms such as a stick, gel, cream, roll-on liquid, pump spray and aerosol spray. A popular form of an antiperspirant product is a gel. Gels can be made transparent (clear), translucent, or opaque. Clear gel antiperspirant compositions are preferred by consumers over opaque compositions for aesthetic reasons. Consumers associate clear transparent products with purity and freshness. Gels also provide a vehicle which glides easily over the surface of the skin resulting in easy and comfortable application of the antiperspirant product to the body. Additionally, clear gel antiperspirant compositions leave less residue or dust on the skin. For clear gel antiperspirants the gelling agents of choice have been the dibenzylidene alditols (e.g., dibenzylidene sorbitol) because they are able to form clear free standing gels. However, dibenzylidene alditols are unstable and degrade in certain formulation environs.

While dibenzylidene alditols are stable in alkaline and neutral media, these compounds are not stable when formulated in the presence of acidic antiperspirant active materials. In an acidic environment they deteriorate and liquefy resulting in a product which has a short self life. Moreover, the residue problem is not totally eliminated in that these compositions still leave a white, staining residue on contacted skin or clothing.

The present invention provides specific polymer gellants which, when utilized with acidic antiperspirant agents provide good opaque to transparent gel properties without the degradation problems that typically accompanies the use of dibenzylidene alditol gelling agents while avoiding a visible residue, e.g., a white layer, that is left on the skin or clothing after the antiperspirant composition is applied.

DESCRIPTION OF EXEMPLARY EMBODIMENTS

Figure 1:
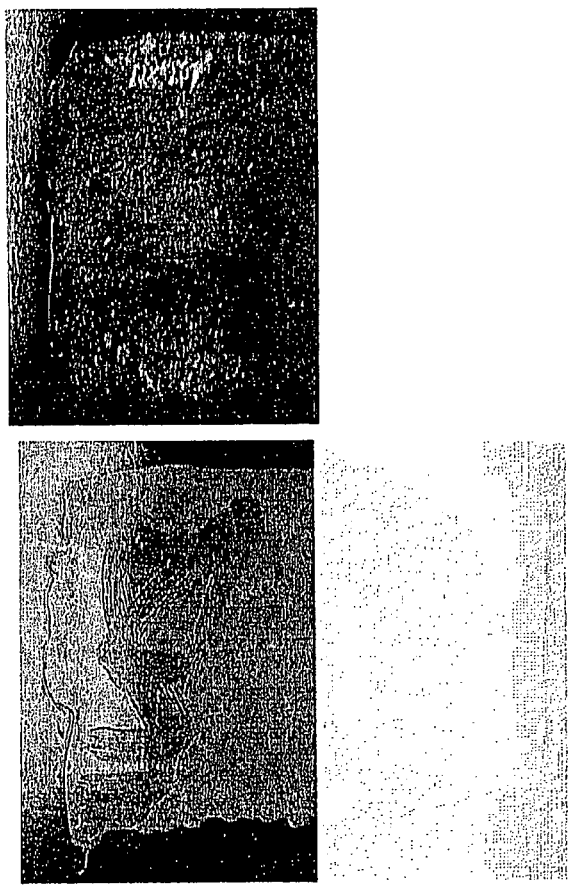
FIG. 1 shows side-by-side comparative photographs of dried commercially available antiperspirant films and the composition of Example 14. The films are drawn across Leneta opacity chart paper and evaluated for residual whitening.

In one aspect, embodiments of the present invention relate to antiperspirant gel compositions comprising:

a) from about 0.1 wt. % to about 10 wt. % (on a polymer solids basis) of a cationic hydrophobically modified polymeric gellant;

b) from about 5 wt. % to about 35 wt. % (on an actives basis) of an acidic antiperspirant agent;

c) from about 5 wt. % to about 95 wt. % water; and optionally d) from about 5 wt. % to about 30 wt. % of an emollient;

e) from about 0.1 wt. % to about 20 wt. % of a monoalcohol;

f) from about 0.1 wt. % to about 10 wt. % of a humectant; and g) from about 0.1 wt. % to about 5 wt. % of an auxiliary gelling agent; all weights are based on the weight of the total antiperspirant composition.

Polymeric Gelling Agent

The polymers suitable for formulating the antiperspirant compositions of the present invention are multifunctional vinyl addition polymers having a combination of amino substituents that provide hydrophilicity and cationic properties at low pH, hydrophobic substituents to attenuate the hydrophilicity, hydrophobically modified polyoxyalkylene substituents that provide associative properties, and hydrophilic polyoxyalkylene substituents that attenuate the associative properties and provide beneficial rheological properties. The polymers are produced by polymerization of a monomer mixture comprising at least one amino-substituted vinyl monomer; at least one hydrophobic nonionic vinyl monomer; at least one associative vinyl monomer; at least one semihydrophobic vinyl surfactant monomer; and, optionally, comprising one or more hydroxy-substituted nonionic vinyl monomer, crosslinking monomer, chain transfer agent, polymeric stabilizer, and the like.

The cationic hydrophobically modified polymers are swelled or thickened upon acidification with the acidic antiperspirant agents described below. Auxiliary acidification agents selected from inorganic acids, organic acids, and combinations thereof can be utilized in combination with the acidic antiperspirants. Alternatively, alkylation agents can be utilized with the acidic antiperspirant agents alone or in combination with the auxiliary acidification agents to induce polymer swelling. The cationic character of the polymers at low pH gives them homogeneity, conditioning and antistatic properties, and under certain conditions, may also provide biocidal, anti-microbial, or other preservative activity.

The polymer gellants of the present invention beneficially can thicken acidic antiperspirant formulations to provide aesthetically smooth-textured products that flow smoothly and spread easily. The form of a polymer containing product can range from a non-pourable, stiff to soft gel, a semisolid paste to a substantially solid stick or bar, and aerosolized foam to squeezable gel, as well as a non-runny, yet flowable, product, suitable for pumpable spray or roll-on products and liquid lotions. It has been surprisingly discovered that the cationic hydrophobically modified polymers provide desirable rheological properties to low pH antiperspirant compositions without leaving a white staining residue following application to the skin. The cationic hydrophobically modified polymers are cationic compatible making them particularly useful as thickeners in antiperspirant products containing quaternary ammonium salts or amines.

The cationic hydrophobically modified polymers of the present invention are prepared by polymerizing a monomer mixture containing: at least one basic, amino-substituted vinyl (ASV) monomer or salt thereof; at least one hydrophobic nonionic vinyl (HNV) monomer; at least one associative vinyl (AV) monomer; at least one semihydrophobic vinyl surfactant (SVS) monomer; and, optionally one or more hydroxy-substituted nonionic vinyl (HSNV) and/or crosslinking (XL) monomer. The cationic hydrophobically modified polymers of the present invention can also be prepared from monomer mixtures containing chain transfer agents (CTA) or other functional components commonly utilized in emulsion polymers and emulsion polymerization processes.

In one aspect of the invention, the cationic hydrophobically modified polymer is the polymerization product of a monomer mixture comprising, on a total monomer mixture weight basis:

a) about 10 to about 70 weight percent of at least one ASV monomer or a salt thereof;

b) about 20 to about 80 weight percent of at least one HNV monomer;

c) about 0.01 to about 25 weight percent of at least one AV monomer;

d) about 0.01 to about 25 weight percent of at least one SVS monomer;

e) up to about 10 weight percent of a HSNV monomer;

f) up to about 5 weight percent of a XL monomer; and g) up to about 10 weight percent of a CTA; and (h) up to about 2 weight percent of a polymeric stabilizer.

In another aspect of the invention, the cationic hydrophobically modified polymer is the polymerization product of a monomer mixture comprising, on a total monomer mixture weight basis:

a) about 25 to about 60 weight percent of at least one ASV monomer or a salt thereof;

b) about 20 to about 70 weight percent of at least one HNV monomer;

c) about 0.1 to about 15 weight percent of at least one AV monomer;

d) about 0.1 to about 10 weight percent of at least one SVS monomer;

e) about 0.1 to about 10 weight percent of HSNV monomer;

f) about 0.001 to about 5 weight percent of a XL monomer; and g) about 0.001 to about 5 weight percent of a CTA.

In one aspect the polymer of the present invention is a polymer that is the product of polymerization of a monomer mixture comprising, on a total monomer mixture weight basis:

a) about 20 to about 50 weight percent of at least one amino-substituted vinyl monomer selected from: 3-(N,N-dimethylamino)propyl (meth)acrylate, and N'-(3-N,N-dimethylamino)propyl (meth)acrylamide. In another aspect the at least one amino-substituted vinyl monomer includes 2-(N,N-dimethylamino)ethyl methacrylate (DMAEMA), 2-(N,N-diethylamino)ethyl methacrylate (DEAEMA), 2-(tert-butylamino)ethyl methacrylate (TBAEMA), 2-(N,N-dimethylamino)propyl methacrylamide (DMAPMAm), and 2-(N,N-dimethylamino)neopentyl acrylate (DMANPA);

b) about 50 to about 65 weight percent of at least one hydrophobic nonionic vinyl monomer selected from $C_1$-$C_{30}$ alkyl ester of acrylic acid, a $C_1$-$C_{30}$ alkyl ester of methacrylic acid, and a mixture thereof;

c) about 0.1 to about 10 weight percent of at least one associative vinyl monomer selected from cetyl polyethoxylated methacrylate (CEM), cetearyl polyethoxylated methacrylate (CSEM), stearyl polyethoxylated (meth)acrylate, arachidyl polyethoxylated (meth)arcylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth)acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM);

d) about 0.1 to about 10 weight percent of at least one semihydrophobic vinyl surfactant monomer having one of the following chemical formulae:

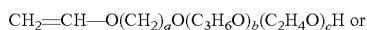

$CH_2\!=\!CH\!-\!O(CH_2)_aO(C_3H_6O)_b(C_2H_4O)_cH$ or

$CH_2\!=\!CHCH_2O(C_3H_6O)_d(C_2H_4O)_eH$;

wherein a is 2, 3, or 4; b is an integer in the range of 1 to about 10; c is an integer in the range of about 5 to about 50; d is an integer in the range of 1 to about 10; and e is an integer in the range of about 5 to about 50;

e) up to about 10 weight percent of a hydroxy-substituted nonionic vinyl monomer;

f) up to about 5 weight percent of a crosslinking monomer;

g) up to about 10 weight percent of a chain transfer agent; and h) up to about 2 weight percent of a polymeric stabilizer.

As used herein the term "alkyl" means a substituted or unsubstituted aliphatic hydrocarbon moiety including linear, branched and carbocyclic alkyl moieties. The term "carbocyclic alkyl" means an alkyl group comprising one or more carbocyclic rings of from 3 to about 12 carbon atoms in size and optionally including alkyl substituents on the carbocyclic ring. The term "aryl" includes substituted and unsubstituted phenyl and naphthyl moieties. Modifiers of the form "$C_x$-$C_y$," designate that the alkyl or carbocyclic alkyl groups have molecular formulas containing a total of x to y carbon atoms, where x and y are specified integers. As used herein and in the appended claims, the term "complex ester" means a di-, tri-, or poly-ester of a polyol such as a sugar, having at least one hydroxyl group capable of being alkylated with a $C_2$-$C_7$ alkylene oxide. The term "complex ester" includes, in particular the complex hydrophobes described in Jenkins et al., in U.S. Pat. No. 5,639,841, the relevant disclosure of which is incorporated herein by reference.

The terms "halogen-substituted", "hydroxy-substituted", "carboxy-substituted", "polyoxyalkylene-substituted", "alkyl-substituted", and "aryl-substituted" as used herein in reference to alkyl or aryl groups, and the like, mean that at least one hydrogen atom on an alkyl, aryl, or like group has been replaced by at least one halogen atom, hydroxyl group, carboxyl group, polyoxyalkylene group, alkyl group, or aryl group, respectively. The terms "poly(meth)acrylate" and "poly(meth)acrylamide" as used herein refer in the alternative to polyacrylate or polymethacrylate, and to polyacrylamide or polymethacrylamide, respectively.

Suitable monomers useful in the preparation of the cationic hydrophobically modified polymers of the present invention are described below.

ASV Monomer

Amino-substituted vinyl monomers suitable for the preparation of the inventive cationic associative polymers are basic, polymerizable, ethylenically unsaturated monomers preferably containing at least one amino functional group. These basic amino groups can be derived from mono-, di- or polyamino alkyl groups or nitrogen containing heteroaromatic groups. The amino group can comprise primary, secondary or tertiary amines. The monomers can be used in the amino form or in the salt form, as desired.

In one aspect the polymers of the present invention include an ASV monomer selected from: a mono-($C_1$-$C_4$)alkylamino ($C_1$-$C_8$)alkyl (meth)acrylate, a di-($C_1$-$C_4$)alkylamino($C_1$-$C_8$) alkyl (meth)acrylate, a mono-($C_1$-$C_4$)alkylamino($C_1$-$C_8$) alkyl (meth)acrylamide, a di-($C_1$-$C_4$)alkylamino($C_1$-$C_8$) alkyl (meth)acrylamide, a nitrogen-containing heterocyclic (meth)acrylamide, a nitrogen-containing heterocyclic (meth) acrylate, and a mixture thereof.

Exemplary ASV monomers include, but are not limited to: a mono- or di-($C_1$-$C_4$)alkylamino($C_1$-$C_4$)alkyl (meth)acrylate, such as 2-(N,N-dimethylamino)ethyl (meth)acrylate,3-(N,N-dimethylamino)propyl (meth)acrylate,4-(N,N-dimethylamino)butyl (meth)acrylate, (N,N-dimethylamino)-t-butyl(meth)acrylate, 2-(N,N-diethylamino)ethyl (meth) acrylate, 3-(N,N-diethylamino)propyl(meth)acrylate, 4-(N,N-diethylamino)butyl(meth)acrylate, 2-(N,N-dipropylamino)ethyl (meth)acrylate, 3-(N,N-dipropylamino) propyl (meth)acrylate, 4-(N,N-dipropylamino)butyl (meth) acrylate, and the like; a mono- or di-($C_1$-$C_4$)alkylamino($C_1$-$C_4$)alkyl (meth)acrylamide such as N'-(2-N,N-dimethylamino)ethyl methacrylamide, N'-(3-N,N-dimethylamino)propyl acrylamide, and the like; and a nitrogen-containing heterocyclic (meth)acrylamide or (meth) acrylate such as N-(2-pyridyl)acrylamide, N-(2-imidazoyl) methacrylamide, 2-(4-morpholinyl)ethyl methacrylate, 2-(4-morpholinyl)ethyl acrylate, N-(4-morpholinyl) methacrylamide, N-(4-morpholinyl)acrylamide, 2-vinyl pyridine, 4-vinyl pyridine, and the like.

The foregoing monomers or salts thereof can be used as the amino-substituted vinyl monomer component of the inventive cationic hydrophobically modified polymers, individually, or in mixtures of two or more. In one aspect of the invention, the ASV monomers are selected from at least one of 2-(N,N-dimethylamino)ethyl (meth)acrylate, 3-(N,N-dimethylamino)propyl (meth)acrylate, and N'-(3-N,N-dimethylamino)propyl (meth)acrylamide. In another aspect the ASV monomers are selected from at least one of 2-(N,N-dimethylamino)ethyl methacrylate (DMAEMA), 2-(N,N-diethylamino)ethyl methacrylate (DEAEMA), 2-(tert-butylamino)ethyl methacrylate (TBAEMA), 2-(N,N-dimethylamino)propyl methacrylamide (DMAPMAm), and 2-(N,N-dimethylamino)neopentyl acrylate (DMANPA).

In one aspect of the invention, the ASV monomer comprises from about 10 to about 70 weight percent of the total monomer mixture, in another aspect from about 20 to about 50 weight percent, and in a further aspect from about 30 to about 40 weight percent, on a total monomer mixture weight basis.

HNV Monomer

Hydrophobic nonionic vinyl monomers suitable for use in the preparation of the inventive cationic hydrophobically modified polymers are copolymerizable, nonionic, ethylenically unsaturated monomers having either of the following formulas (I) or (II):

$$CH_2=C(X)Z, \quad (I)$$

$$CH_2=CH-OC(O)R; \quad (II)$$

wherein, in each of formulas (I) and (II), X is H or methyl; and Z is —C(O)O$R^1$, —C(O)N$H_2$, —C(O)NH$R^1$, —C(O)N($R^1$)$_2$, —$C_6H_4R^1$, —$C_6H_4OR^1$, —$C_6H_4CL$, —CN, —NHC(O)C$H_3$, —NHC(O)H, N-(2-pyrrolidonyl), N-caprolactamyl, —C(O)NHC(C$H_3$)$_3$, —C(O)NHC$H_2$C$H_2$—N-ethyleneurea, —Si$R_3$, —C(O)O(C$H_2$)$_x$Si$R_3$, —C(O)NH(C$H_2$)$_x$Si$R_3$, or —(C$H_2$)$_x$Si$R_3$; x is an integer in the range of 1 to about 6; each R is independently $C_1$-$C_{30}$ alkyl; each $R^1$ is independently $C_1$-$C_{30}$ alkyl, hydroxy-substituted $C_2$-$C_{30}$ alkyl or halogen-substituted $C_1$-$C_{30}$ alkyl.

Non-limiting examples of hydrophobic nonionic vinyl monomers include $C_1$-$C_{30}$ alkyl (meth)acrylates; $C_1$-$C_{30}$ alkyl (meth)acrylamides; styrene; substituted styrenes such as vinyl toluene, (e.g., 2-methyl styrene), butyl styrene, isopropyl styrene, p-chloro styrene, and the like; vinyl esters such as vinyl acetate, vinyl butyrate, vinyl caprolate, vinyl pivalate, vinyl neodecanoate, and the like; unsaturated nitriles such as methacrylonitrile, acrylonitrile and the like; and unsaturated silanes such as trimethylvinylsilane, dimethylethylvinylsilane, allyldimethylphenylsilane, allytrimethylsilane, 3-acrylamidopropyltrimethylsilane, 3-trimethylsilyl-propyl methacrylate, and the like.

In one aspect of the invention, the nonionic vinyl monomers include $C_1$-$C_{30}$ alkyl esters of acrylic acid and of methacrylic acid and mixtures thereof, examples of which include but are not limited to ethyl acrylate (EA), methyl methacrylate (MMA), 3,3,5-trimethylcyclohexyl methacrylate (TMCHMA), and mixtures thereof.

In one aspect of the invention, the HNV monomer comprises from about 20 to about 80 weight percent of the total monomer mixture, in another aspect from about 30 to about 70 weight percent, and in a further aspect from about 50 to about 65 weight percent, on a total monomer mixture weight basis.

AV Monomer

Associative vinyl monomers suitable for use in the production of the cationic hydrophobically modified polymers are compounds having an ethylenically unsaturated end group portion (i) for addition polymerization with the other monomers of the system; a polyoxyalkylene midsection portion (ii) for imparting selective hydrophilic properties to the product polymer and a hydrophobic end group portion (iii) for providing selective hydrophobic properties to the polymer.

The portion (i) supplying the ethylenically unsaturated end group can be derived from an ethylenically unsaturated mono or di-carboxylic acid or the anhydride thereof. In one aspect the ethylenically unsaturated end group can be derived from a $C_3$ or $C_4$ mono- or di-carboxylic acid or the anhydride thereof. Alternatively, portion (i) of the associative monomer can be derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The midsection portion (ii) is a polyoxyalkylene segment of from about 5 to about 250 units in one aspect, from about 10 to about 120 units in another aspect, and from about 15 to about 60 units in a further aspect of repeating $C_2$-$C_7$ alkylene oxide units. Exemplary midsection portions (ii) include polyoxyethylene, polyoxypropylene, and polyoxybutylene segments comprising from about 5 to about 150 units in one aspect, from about 10 to about 100 units in another aspect, and from about 15 to about 60 units in a further aspect of ethylene, propylene or butylene oxide repeating units. In still another aspect of the invention, the ethylene oxide, propylene oxide and/or butylene oxide units can be situated as random or non-random sequences on the same segment.

The hydrophobic end group portion (iii) of the associative monomers is can be selected from a hydrocarbon moiety belonging to one of the following hydrocarbon classes: a $C_8$-$C_{40}$ linear alkyl, an aryl-substituted $C_2$-$C_{40}$ alkyl, a $C_2$-$C_{40}$ alkyl-substituted phenyl, a $C_8$-$C_{40}$ branched alkyl, a $C_8$-$C_{40}$ carbocyclic alkyl; and a $C_8$-$C_{80}$ complex ester.

Non-limiting examples of suitable hydrophobic end group portions (iii) of the associative monomers are linear or branched alkyl groups having about 8 to about 40 carbon atoms such as capryl ($C_8$), isooctyl (branched $C_8$), decyl ($C_{10}$), lauryl ($C_{12}$), myristyl ($C_{14}$), cetyl ($C_{16}$), cetearyl ($C_{16}$-$C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), lacceryl ($C_{32}$), and the like.

Examples of linear and branched alkyl groups having about 8 to about 40 carbon atoms that are derived from a natural source include, without being limited thereto, alkyl groups derived from hydrogenated peanut oil, soybean oil and canola oil (all predominately $C_{18}$), hydrogenated tallow oil ($C_{16}$-$C_{18}$), and the like; and hydrogenated $C_{10}$-$C_{30}$ terpenols, such as hydrogenated geraniol (branched $C_{10}$), hydrogenated farnesol (branched $C_{15}$), hydrogenated phytol (branched $C_{20}$), and the like.

Non-limiting examples of suitable $C_2$-$C_{40}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Suitable $C_8$-$C_{40}$ carbocyclic alkyl groups include, but are not limited to groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials such as pinene, hydrogenated retinol, camphor, isobornyl alcohol, and the like.

Exemplary aryl-substituted $C_2$-$C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Non-limiting examples of suitable $C_8$-$C_{80}$ complex esters include hydrogenated castor oil (predominately the triglyceride of 12-hydroxystearic acid); 1,2-diacyl glycerols such as 1,2-distearyl glycerol, 1,2-dipalmityl glycerol, 1,2-dimyristyl glycerol, and the like; di-, tri-, or poly-esters of sugars such as 3,4,6-tristearyl glucose, 2,3-dilauryl fructose, and the like; and sorbitan esters such as those disclosed in U.S. Pat. No. 4,600,761 to Ruffner et al., the pertinent disclosures of which are incorporated herein by reference.

Useful associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, III et al.; the pertinent disclosures of which are incorporated herein by reference.

Examples of preferred associative vinyl monomers include those having the following formula (III):

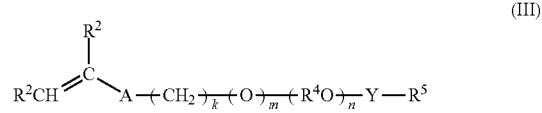

(III)

wherein, each $R^2$ is independently H, methyl, —C(O)OH, or —C(O)$OR^3$; $R^3$ is $C_1$-$C_{30}$ alkyl; A is —$CH_2$C(O)O—, —C(O)O—, —O—, —$CH_2$O—, —NHC(O)NH—, —C(O)NH—, —Ar—$(CE_2)_z$—NHC(O)O—, —Ar—$(CE_2)_z$—NHC(O)NH—, or —$CH_2CH_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; $(R^{40})_n$ is a polyoxyalkylene, which is a homopolymer, a random copolymer, or a block copolymer of $C_2$-$C_4$ oxyalkylene units, wherein $R^4$ is —$C_2H_4$—, —$C_3H_6$—, —$C_4H_8$—, or a mixture thereof, and n is an integer in the range of about 5 to about 250, preferably about 5 to about 100, more preferably about 10 to about 80, and most preferably about 15 to about 60; Y is —$R^{40}$—, —$R^4$NH—, —C(O)—, —C(O)NH—, —$R^4$NHC(O)NH—, or —C(O)NHC(O)—; and $R^5$ is a substituted or unsubstituted alkyl selected from the group consisting of a $C_8$-$C_{40}$ linear alkyl, a $C_8$-$C_{40}$ branched alkyl, a $C_8$-$C_{40}$ carbocyclic alkyl, a $C_2$-$C_{40}$ alkyl-substituted phenyl, an aryl-substituted $C_2$-$C_{40}$ alkyl, and a $C_8$-$C_{80}$ complex ester; wherein the $R^5$ alkyl group optionally comprises one or more substituents selected from the group consisting of a hydroxyl group, an alkoxyl group, and a halogen group.

In one aspect of the invention the associative vinyl monomers of formula (III) include cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), where the polyethoxylated portion of the monomer comprises about 5 to about 100, preferably about 10 to about 80, and more preferably about 15 to about 60 ethylene oxide repeating units.

In one aspect the AV monomer component in the monomer mixture comprises, on a total monomer mixture weight basis, from about 0.001 to about 25 weight percent of the monomer mixture, in another aspect from about 0.01 to about 15 weight percent, and in a further aspect from about 0.1 to about 10 weight percent.

SVS Monomer

It was surprisingly found that a semihydrophobic vinyl surfactant (SVS) monomer, which contains a polyoxyalkylene chain, can moderate the associative properties of cationic hydrophobically modified polymers containing them, thus producing aqueous gels with highly desirable texture and rheological properties. Not wishing to be bound by theory, it is thought that the polyoxyalkylene group of the SVS monomer interrupts or shields against non-specific associations between the hydrophobic groups of the associative monomers in the polymer and thus attenuates the associative properties of the polymers. Such SVS monomers can tailor the thickening efficiency of the resulting polymers to customize the rheological properties of the polymer as desired for a selected application. Most surprisingly, the SVS monomers were found to impart desirable rheological and aesthetic properties to aqueous gels, providing softer, smoother and more spreadable gels than cationic hydrophobically modified polymers containing no SVS monomer.

As used herein the terms "semihydrophobic vinyl surfactant monomer" and "SVS monomer" refer to compounds having two portions: (i) an ethylenically unsaturated end group portion for addition polymerization with the other monomers of the reaction mixture, and (ii) a polyoxyalkylene portion for attenuating the associations between the hydrophobic groups of the polymer or hydrophobic groups from other materials in a composition containing the polymer. A SVS monomer is similar in structure to an associative monomer, but has a substantially non-hydrophobic end group portion and thus, does not impart any associative properties to the polymer.

The unsaturated end group portion (i) supplying the vinyl or other ethylenically unsaturated end group for addition polymerization is preferably derived from an ethylenically unsaturated mono or di-carboxylic acid or the anhydride thereof, preferably a $C_3$ or $C_4$ mono- or di-carboxylic acid, or the anhydride thereof. Alternatively, the end group portion (i) can be derived from an allyl ether, vinyl ether or a nonionic unsaturated urethane.

The polymerizable unsaturated end group portion (i) can also be derived from a $C_8$-$C_{30}$ unsaturated fatty acid group containing at least one free carboxy-functional group. This $C_8$-$C_{30}$ group is part of the unsaturated end group portion (i) and is different from the hydrophobic groups pendant to the associative monomers, which are specifically separated from the unsaturated end group of the associative monomer by a hydrophilic "spacer" portion.

The polyoxyalkylene portion (ii) specifically comprises a long-chain polyoxyalkylene segment, which is substantially similar to the hydrophilic portion of the associative monomers. In one aspect of the invention the polyoxyalkylene portion (ii) includes polyoxyethylene, polyoxypropylene, and polyoxybutylene segments comprising from about 5 to about 250 units, and in another aspect from about 10 to about 100 oxyalkylene units. When the SVS monomer comprises more than one type of oxyalkylene unit, the units can be arranged in random, non-random, or block sequences.

In one aspect of the invention SVS monomers include those having either of the following formulas (IV) or (V):

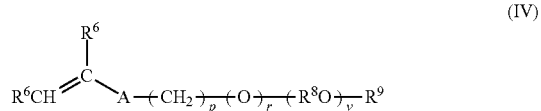

(IV)

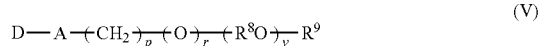

(V)

wherein, in each of formulas (IV) and (V), each $R^6$ is independently H, $C_1$-$C_{30}$ alkyl, —C(O)OH, or —C(O)OR$^7$; $R^7$ is $C_1$-$C_{30}$ alkyl; A is —CH$_2$C(O)O—, —C(O)O—, —O—, —CH$_2$O—, —NHC(O)NH—, —C(O)NH—, —Ar—(CE$_2$)$_z$ —NHC(O)O—, —Ar—(CE$_2$)$_z$—NHC(O)NH—, or —CH$_2$CH$_2$NHC(O)—; Ar is a divalent aryl; E is H or methyl; z is 0 or 1; p is an integer in the range of 0 to about 30, and r is 0 or 1, with the proviso that when p is 0, r is 0, and when p is in the range of 1 to about 30, r is 1; $(R^8O)_v$ is a polyoxyalkylene, which is a homopolymer, a random copolymer or a block copolymer of $C_2$-$C_4$ oxyalkylene units, wherein $R^8$ is —C$_2$H$_4$—, —C$_3$H$_6$—, —C$_4$H$_8$—, or a mixture thereof, and v is an integer in the range of about 5 to about 250 in one aspect, from about 5 to about 100 in another aspect, from about 10 to about 80 in a further aspect, and from about 15 to about 60 in a still further aspect; $R^9$ is H or $C_1$-$C_4$ alkyl; and D is a $C_8$-$C_{30}$ unsaturated alkyl, or a carboxy-substituted $C_8$-$C_{30}$ unsaturated alkyl.

In one aspect of the invention the SVS monomers include monomers having the following chemical formulae:

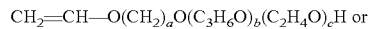

wherein a is an integer of 2, 3, or 4; b is an integer in the range of from 1 to about 10 in one aspect, from about 2 to about 8 in another aspect, and from about 3 to about 7 in a further aspect; c is an integer in the range of from about 5 to about 50 in one aspect, from about 8 to about 40 in another aspect, and from about 10 to about 30 in a further aspect; d is an integer in the range of 1 to about 10 in one aspect, from about 2 to about 8 in another aspect, and from about 3 to about 7 in a further aspect; and e is an integer in the range of from about 5 to about 50 in one aspect, and from about 8 to about 40 in a further aspect of the invention.

Examples of SVS monomers include but are not limited to polymerizable emulsifiers commercially available under the trade names EMULSOGEN® R109, R208, R307, RAL109, RAL208, and RAL307 sold by Clariant Corporation; BX-AA-E5P5 sold by Bimax, Inc.; and MAXEMUL® 5010 and 5011 sold by Uniqema; and combinations thereof. In one aspect of the invention SVS monomers include EMULSOGEN® R208, R307, and RAL307.

According to the manufacturers: EMULSOGEN® R109 is a randomly ethoxylated/propoxylated 1,4-butanediol vinyl ether having the empirical formula CH$_2$=CH—O(CH$_2$)$_4$O (C$_3$H$_6$O)$_4$(C$_2$H$_4$O)$_{10}$H;

EMULSOGEN® R208 is a randomly ethoxylated/propoxylated 1,4-butanediol vinyl ether having the empirical formula:

CH$_2$=CH—O(CH$_2$)$_4$O(C$_3$H$_6$O)$_4$(C$_2$H$_4$O)$_{20}$H;

EMULSOGEN® R307 is a randomly ethoxylated/propoxylated 1,4-butanediol vinyl ether having the empirical formula: CH$_2$=CH—O(CH$_2$)$_4$O(C$_3$H$_6$O)$_4$(C$_2$H$_4$O)$_{30}$H;

EMULSOGEN® RAL109 is a randomly ethoxylated/propoxylated allyl ether having the empirical formula: CH$_2$=CHCH$_2$O(C$_3$H$_6$O)$_4$(C$_2$H$_4$O)$_{10}$H;

EMULSOGEN® RAL208 is a randomly ethoxylated/propoxylated allyl ether having the empirical formula: CH$_2$=CHCH$_2$O(C$_3$H$_6$O)$_4$(C$_2$H$_4$O)$_{20}$H;

EMULSOGEN® RAL307 is a randomly ethoxylated/propoxylated allyl ether having the empirical formula: CH$_2$=CHCH$_2$O(C$_3$H$_6$O)$_4$(C$_2$H$_4$O)$_{30}$H;

MAXEMUL® 5010 is a carboxy-functional $C_{12}$-$C_{15}$ alkenyl hydrophobe, ethoxylated with about 24 ethylene oxide units;

MAXEMUL® 5011 is a carboxy-functional $C_{12}$-$C_{15}$ alkenyl hydrophobe, ethoxylated with about 34 ethylene oxide units; and BX-AA-E5P5 is a randomly ethoxylated/propoxylated allyl ether having the empirical formula: CH$_2$=CHCH$_2$O (C$_3$H$_6$O)$_5$(C$_2$H$_4$O)$_5$H.

The amount of SVS monomers utilized in the preparation of the cationic hydrophobically modified polymers of the present invention can vary widely and depends, among other things, on the final rheological properties desired in the polymer. In one aspect, the reaction mixture contains at least about 0.01 weight percent of one or more SVS monomers based on the total monomer mixture weight, and in another aspect at least about 0.1 weight percent. In a further aspect, the monomer mixture comprises not more than about 25 weight percent of SVS monomer, and in another aspect not more than about 10 weight percent, based on the total monomer mixture weight.

HSNV Monomer

The cationic hydrophobically modified polymers can optionally be prepared from monomer mixtures containing hydroxy-substituted nonionic vinyl monomers (HSNV). HSNV monomers are ethylenically unsaturated monomers comprising one or more hydroxyl substituents.

Examples of suitable HSNV monomers include, but are not limited to, a hydroxy-substituted ($C_1$-$C_4$)alkyl (meth)acrylate such as 2-hydroxyethyl methacrylate (HEMA), 2-hydroxyethyl acrylate (2-HEA), 3-hydroxypropyl acrylate, and the like; a hydroxy-substituted ($C_1$-$C_4$)alkyl (meth)acrylamide such as N-(2-hydroxyethyl)methacrylamide, N-(2-hydroxyethyl)acrylamide, N-(3-hydroxypropyl)acrylamide, N-(2,3-dihydroxypropyl)acrylamide, and the like. Other useful HSNV monomers include allyl alcohol, glycerol monoallyl ether, 3-methyl-3-buten-1-ol, and vinyl alcohol precursors and equivalents, such as vinyl acetate.

When utilized, the monomer reaction mixture contains one or more HSNV monomers in amounts up to about 10 weight percent based on the total monomer mixture weight. In one aspect of the invention the amount of HSNV monomer in the mixture ranges from about 0.01 to about 10 weight percent based on the total monomer mixture weight, in another aspect from about 1 to about 8 weight percent, and in a further aspect from about 1 to about 5 weight percent.

XL Monomer

The cationic hydrophobically modified polymers can be prepared from a monomer mixture comprising one or more crosslinking monomers for introducing branching and controlling molecular weight. Suitable polyunsaturated crosslinkers are well known in the art. Mono-unsaturated compounds carrying a reactive group that is capable of causing a formed copolymer to be crosslinked before, during, or after polymerization has taken place can also be utilized. Other useful crosslinking monomers include polyfunctional monomers containing multiple reactive groups such as epoxide groups, isocyanate groups, and hydrolyzable silane groups. Various polyunsaturated compounds can be utilized to generate either a partially or substantially crosslinked three dimensional network.

Examples of suitable polyunsaturated crosslinking monomer components include, but are not limited to, polyunsaturated aromatic monomers such as divinylbenzene, divinyl naphthylene, and trivinylbenzene; polyunsaturated alicyclic monomers, such as 1,2,4-trivinylcyclohexane; difunctional esters of phthalic acid such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated crosslinking monomers include polyalkenyl ethers such as triallyl pentaerythritol, diallyl pentaerythritol, diallyl sucrose, octaallyl sucrose, and trimethylolpropane diallyl ether; polyunsaturated esters of polyalcohols or polyacids such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, and triethyleneglycol di(meth)acrylate; polyunsaturated silanes, such as dimethyldivinylsilane, methyltrivinylsilane, allyldimethylvinylsilane, diallyidimethylsilane, and tetravinylsilane; polyunsaturated stannanes, such as tetraallyl tin, and diallyldimethyl tin; and the like.

Useful monounsaturated compounds carrying a reactive group include N-methylolacrylamide; N-alkoxy(meth)acrylamide, wherein the alkoxy group is a $C_1$-$C_{18}$ alkoxy; and unsaturated hydrolyzable silanes such as triethoxyvinylsilane, tris-isopropoxyvinylsilane, and 3-triethoxysilylpropyl methacrylate; and the like.

Useful polyfunctional crosslinking monomers containing multiple reactive groups include, but are not limited to, hydrolyzable silanes such as ethyltriethoxysilane and ethyltrimethoxysilane; epoxy-substituted hydrolyzable silanes, such as 2-(3,4-epoxycyclohexyl)ethyltriethoxysilane and 3-glycidoxypropyltrimethyloxysilane; polyisocyanates, such as 1,4-diisocyanatobutane, 1,6-diisocyanatohexane, 1,4-phenylenediisocyanate, and 4,4'-oxybis(phenyl)socyanate); unsaturated epoxides, such as glycidyl methacrylate and allylglycidyl ether; polyepoxides, such as diglycidyl ether, 1,2,5,6-diepoxyhexane, and ethyleneglycoldiglycidyl ether; and the like.

Particularly useful are polyunsaturated crosslinkers derived from ethoxylated polyols, such as diols, triols and bis-phenols, ethoxylated with about 2 to about 100 moles of ethylene oxide per mole of hydroxyl functional group and end-capped with a polymerizable unsaturated group such as a vinyl ether, allyl ether, acrylate ester, methacrylate ester, and the like. Examples of such crosslinkers include bisphenol A ethoxylated dimethacrylate; bisphenol F ethoxylated dimethacrylate, ethoxylated trimethylol propane trimethacrylate, and the like. Other ethoxylated crosslinkers useful in the cationic hydrophobically modified polymers of the present invention include ethoxylated polyol-derived crosslinkers disclosed in U.S. Pat. No. 6,140,435 to Zanotti-Russo, the pertinent disclosures of which are incorporated herein by reference.

Examples of particularly preferred XL monomers are acrylate and methacrylate esters of polyols having at least two acrylate or methacrylate ester groups, such as trimethylolpropane triacrylate (TMPTA), trimethylolpropane dimethacrylate, triethylene glycol dimethacrylate (TEGDMA), ethoxylated (30) bisphenol A dimethacrylate (EOBDMA), and the like.

When utilized, crosslinking monomers are present in the monomer reaction mixture in an amount of up to about 5 weight percent, based on total monomer mixture weight. In one aspect, the XL monomers are present in an amount in the range from about 0.01 to about 3 weight percent, based on the total monomer mixture weight, in another aspect from about 0.05 to about 2 weight percent, and in a further aspect from about 0.1 to about 1 weight percent of the monomer mixture.

Chain Transfer Agent

The inventive cationic hydrophobically modified polymers can optionally be prepared from a monomer mixture comprising one or more chain transfer agents, which are well known in the polymer arts.

Suitable chain transfer agents for use in this invention, without limitation, are selected from a variety of thio and disulfide containing compounds, such as $C_1$-$C_{18}$ alkyl mercaptans, mercaptocarboxylic acids, mercaptocarboxylic esters, thioesters, $C_1$-$C_{18}$ alkyl disulfides, aryldisulfides, polyfunctional thiols, and the like; phosphites and hypophosphites; haloalkyl compounds, such as carbon tetrachloride, bromotrichloromethane, and the like; and unsaturated chain transfer agents, such as alpha-methylstyrene.

Polyfunctional thiols include trifunctional thiols, such as trimethylolpropane-tris-(3-mercaptopropionate), tetrafunctional thiols, such as pentaerythritol-tetra-(3-mercaptopropionate), pentaerythritol-tetra-(thioglycolate), and pentaerythritol-tetra-(thiolactate); hexafunctional thiols, such as dipentaerythritol-hexa-(thioglycolate); and the like.

Alternatively, the chain transfer agent can be any catalytic chain transfer agent which reduces molecular weight of addition polymers during free radical polymerization of vinyl monomers. Examples of catalytic chain transfer agents include, for example, cobalt complexes (e.g., cobalt (II) chelates). Catalytic chain transfer agents can often be utilized in relatively low concentrations relative to thiol-based CTAs.

Examples of preferred chain transfer agents include octyl mercaptan, n-dodecyl mercaptan, t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, dodecyl thioglycolate, and the like. The chain transfer agents can be added to a monomer reaction mixture in amounts of up to about 10 weight percent of polymerizable monomer mixture, based on total monomer mixture weight. In one aspect, when present, the chain transfer agent comprises at least about 0.1 percent by weight based on the total monomer weight.

The inventive cationic hydrophobically modified polymers can be manufactured by conventional polymerization techniques, such as, for example, by emulsion polymerization, as is known in the polymer art. The polymerization can be performed as a simple batch process, as a metered addition process, or the reaction can be initiated as a small batch and then the bulk of the monomers can be continuously metered into the reactor (seed process). Typically the polymerization process is carried out at a reaction temperature in the range of about 20 to about 80° C., however, higher or lower temperatures can be used. To facilitate emulsification of the monomer mixture, the emulsion polymerization is carried out in the presence of at least one surfactant. Preferably the emulsion polymerization is carried out in the presence of surfactant in the amount of about 1 to about 10 percent by weight, more preferably in the range of about 3 to about 8, most preferably in the range of about 5 to about 7 percent by weight, on a total emulsion weight basis. The emulsion polymerization reaction mixture also includes one or more free radical initiators, preferably in an amount in the range of about 0.01 to about 3 weight percent based on total monomer weight. The polymerization can be performed in an aqueous or aqueous alcohol medium at neutral to moderately alkaline pH.

In a typical polymerization, a mixture of the disclosed monomers is added with mixing agitation to a solution of emulsifying surfactant, such as a nonionic surfactant, preferably a linear or branched alcohol ethoxylate, or mixtures of nonionic surfactants and anionic surfactants, such as fatty alcohol sulfates or alkyl sulfonates, in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The reaction is agitated until the polymerization is complete, typically for a time in the range of about 4 to about 16 hours. The monomer emulsion can be heated to a temperature in the range of about 20 to about 80° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 40 weight percent. Typically, the total polymer content of the product emulsion is in the range of about 15 to about 35 weight percent, generally not more than about 25 weight percent.

Suitable surfactants for facilitating emulsion polymerizations include nonionic, anionic, amphoteric, cationic surfactants, and mixtures thereof. Most commonly, nonionic and anionic surfactants are utilized or mixtures thereof. The physical properties of the neutralized polymer (e.g., viscosity, spreadability, clarity, texture, and the like) can be varied by appropriate selection of the hydrophobic and hydrophilic properties of the emulsifying surfactant, as is well known in the art.

Nonionic surfactants suitable for facilitating emulsion polymerizations are well known in the polymer art, and include, without limitation, linear or branched alcohol ethoxylates, $C_8$-$C_{12}$ alkylphenol alkoxylates, such as octylphenol ethoxylates, polyoxyethylene polyoxypropylene block copolymers, and the like. Other useful nonionic surfactants include $C_8$-$C_{22}$ fatty acid esters of polyoxyethylene glycol, mono and diglycerides, sorbitan esters and ethoxylated sorbitan esters, $C_8$-$C_{22}$ fatty acid glycol esters, block copolymers of ethylene oxide and propylene oxide having an HLB value of greater than about 15, ethoxylated octylphenols, and combinations thereof.

Exemplary alkylphenol alkoxylate surfactants include an octylphenol sold under the trade name IGEPAL® CA-897 by Rhodia, Inc. Exemplary linear alcohol alkoxylates include polyethylene glycol ethers of cetearyl alcohol (a mixture of cetyl and stearyl alcohols) sold under the trade names PLURAFAC® C-17, PLURAFAC® A-38 and PLURAFAC® A-39 by BASF Corp. Exemplary polyoxyethylene polyoxypropylene block copolymers include copolymers sold under the trade names PLURONIC® F127, and PLURONIC® L35 by BASF Corp.

Other Exemplary nonionic surfactants include Ethoxylated (50) linear fatty alcohols such as DISPONIL® A 5060 (Cognis), branched alkyl ethoxylates such as GENAPOL® X 1005 (Clariant Corp.), secondary $C_{12}$-$C_{14}$ alcohol ethoxylates such as TERGITOL® S15-30 and S15-40 (Dow Chemical Co.), ethoxylated octylphenol-based surfactants such as TRITON® X-305, X-405 and X-705 (Dow Chemical Co.), IGEPAL® CA 407, 887, and 897 (Rhodia, Inc.), ICONOL® OP 3070 and 4070 (BASF Corp.), SYNPERONIC® OP 30 and 40 (Uniqema), block copolymers of ethylene oxide and propylene oxide such as PLURONIC® L35 and F127 (BASF Corp.), and secondary $C_{11}$ alcohol ethoxylates such as EMULSOGEN® EPN 407 (Clariant Corp.). Numerous other suppliers are found in the trade literature.

Anionic surfactants suitable for facilitating emulsion polymerizations are well known in the polymer art, and include sodium lauryl sulfate, sodium dodecyl benzene sulfonate, sodium dioctyl sulfosuccinate, sodium di-sec-butyl naphthylene sulfonate, disodium dodecyl diphenyl ether sulfonate, and disodium n-octadecyl sulfosuccinate, and the like.

Suitable polymeric stabilizers (also known as protective colloids) for the emulsion polymerization process of this invention are water-soluble polymers, including, for example, synthetic polymers, such as polyvinyl alcohol, partially hydrolyzed polyvinyl acetate, polyvinylpyrrolidone, polyacrylamide, polymethacrylamide, carboxylate-functional addition polymers, polyalkyl vinyl ethers and the like; water-soluble natural polymers, such as gelatin, pectins, alginates, casein, starch, and the like; and modified natural polymers, such as methylcellulose, hydroxypropylcellulose, carboxymethylcellulose, allyl modified hydroxyethylcellulose, and the like. In some cases, it can be of advantage to use mixtures of a synthetic and a natural protective colloid, for example, a mixture of polyvinyl alcohol and casein. Further suitable natural polymers are mixed ethers such as methylhydroxyethylcellulose and carboxymethylmethylcellulose. Polymeric stabilizers can be utilized in amounts up to about 2 weight percent based on the total emulsion weight. When utilized, a polymeric stabilizer can be included in an amount in the range of about 0.0001 to about 1 weight percent, more preferably about 0.01 to about 0.5 weight percent.

The polymeric stabilizers which are used according to this invention are termed water-soluble when they are miscible in water in any proportion or have a solubility in 20° C. water of at least about 0.1% by weight and do not precipitate from these aqueous solutions on dilution with water at the foregoing temperature. The molecular weight of the water-soluble synthetic polymeric stabilizers is typically in the range of from about 5,000 to about 2,000,000 Daltons in one aspect, and from about 25,000 to about 1,500,000 Daltons in another aspect. The viscosity of aqueous solutions of the polymeric stabilizers is typically in the range of about 1 to about 10,000 mPa·s at a concentration of about 2 to about 10% by weight and a temperature of about 20° C.

In one aspect of polymer manufacture, the polymeric stabilizer is selected from an allyl modified hydroxyethylcellulose, such as TYLOSE® AM-HEC grades available from Clariant. The reactive allyl groups in the side chain increase the grafting power of the cellulose ether resulting in a stable emulsion. A preferred TYLOSE® stabilizer is allyl modified hydroxyethylcellulose powder (particle size <180 μm) TYLOSE® AM H40 YP2 (AMHEC).

Exemplary free radical initiators include, without being limited thereto, the water-soluble inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid; and oil soluble, free radical producing agents, such as 2,2'-azobisisobutyronitrile, and the like, and mixtures thereof. Peroxides and peracids can optionally be activated with reducing agents, such as sodium bisulfite or ascorbic acid, transition metals, hydrazine, and the like. Particularly suitable free-radical polymerization initiators include water soluble azo polymerization initiators, such as 2,2'-azobis (tert-alkyl) compounds having a water solubilizing substituent on the alkyl group. Preferred azo polymerization catalysts include the VAZO® free-radical polymerization initiators, available from DuPont, such as VAZO® 44 (2,2'-azobis(2-(4, 5-dihydroimidazolyl)propane), VAZO® 56 (2,2'-azobis(2-methylpropionamidine) dihydrochloride), and VAZO® 68 (4,4'-azobis(4-cyanovaleric acid)).

Optionally, other emulsion polymerization additives, which are well known in the emulsion polymerization art, such as solvents, buffering agents, chelating agents, inorganic electrolytes, chain terminators, and pH adjusting agents can be included in the polymerization system.

An exemplary general emulsion polymerization procedure for the preparation of the cationic hydrophobically modified polymers of the present invention and of cationic emulsion polymers, in general, is provided below.

A monomer emulsion is prepared in a reactor equipped with a nitrogen inlet and an agitator by combining a desired amount of each monomer in a quantity of water containing an emulsifying amount of a nonionic surfactant, or a mixture of a nonionic surfactant and an anionic surfactant, under a nitrogen atmosphere, and with mixing agitation. The degree of agitation required to form an emulsion from a monomer mixture of the type described above is well known to those of skill in the art. The so-formed emulsion is substantially deoxygenated by any suitable method known in the art, such as by sparging with nitrogen, and then a free radical initiator is added to the emulsion, with continuous mixing agitation, to initiate polymerization. The temperature of the emulsion can be adjusted, before or after addition of the initiator, to a temperature in the range of about 20 to about 60° C. if desired. After the addition of initiator, the temperature of the polymerization reaction mixture is typically adjusted to a temperature in the range of about 60 to 80° C. and held at such temperature for a time sufficient to complete the polymerization, typically in the range of about 3 to about 14 hours. Optionally, unreacted residual monomers can be destroyed or further polymerized by the addition of various redox reagents or catalysts. The resulting polymer emulsion can then be cooled and discharged from the reactor and collected.

One skilled in the polymer art will recognize that the amounts of each monomer component can be adjusted to obtain polymers having any desired ratio of monomer components. Varying proportions of water can also be utilized, as desired. Water miscible solvents, such as alcohols, and other polymerization additives, as described above, may also be included in the reaction mixture. Preferred alcohols include glycols such as ethylene glycol, propylene glycol, butylene glycol, hexylene glycol, glycerol, and the like.

The product polymer emulsions can be prepared to contain from about 1 percent to about 60 percent total polymer solids in one aspect, from about 10 percent to about 40 percent total polymer solids in another aspect, and from about 15 percent to about 25 percent total polymer solids in a further aspect based on the weight of the polymer.

Prior to any neutralization, the polymer emulsions, as produced, typically have a pH in the range of about 7.5 or greater, a Brookfield viscosity of not more than about 100 mPa·s at ambient room temperature (spindle #2, 20 rpm), and a particle size of not more than about 300 nm.

Optionally, the produced cationic hydrophobically modified polymer emulsions can be further processed by adjusting the pH to a value preferably in the range of about 1 to not more than about 7, if an acidic pH is desired, with acidic materials, such as, for example, the acidic antiperspirant agents alone or in combination with auxiliary acidification agents selected from inorganic acids, organic acids, and combinations thereof. The cationic hydrophobically modified polymer emulsions typically swell to form smooth, viscous solutions that are flowable and sprayable, or gels at neutral to acidic pH, and the polymers are generally substantially stable at such pH values. The cationic hydrophobically modified polymer emulsions can be diluted with water or solvent, or concentrated by evaporating a portion of the water.

In one aspect of the invention a polymer suitable for use in the formulations of the invention are commercially available from Noveon, Inc. under the Aqua CC™ trade name (INCI Name: Polyacrylate-1 Crosspolymer).

The cationic hydrophobically modified polymers can be utilized by incorporating various known additives and conventional adjuvants, and solvents other than water, into the liquid cationic hydrophobically modified polymer emulsion product, as needed, to achieve the intended form for use of the final composition without altering or adversely affecting the performance or properties of the cationic hydrophobically modified polymer. Alternatively, the cationic hydrophobically modified polymer can be incorporated as an ingredient into a formulation, preferably in a liquid form, employing conventional mixing equipment.

While a primary aspect of the invention is directed to antiperspirant gel compositions, there is no limitation as to the form of product in which the cationic hydrophobically modified polymer can be incorporated, so long as the purpose for which the product is used is achieved. Accordingly, the antiperspirant compositions can be formulated in the form of, without limitation, gels, solids (sticks), liquids (sprays), emulsions (creams, lotions, pastes), and the like.

The amount of cationic hydrophobically modified polymer that is employed in a particular antiperspirant formulation depends upon the intended delivery form of the antiperspirant product and can be readily determined by a person skilled in the antiperspirant formulation arts. Thus any amount of the cationic hydrophobically modified polymer can be utilized as long as the physicochemical and functional properties of the antiperspirant compositions containing the polymer are achieved. In a given composition or application the cationic hydrophobically modified polymers of this invention can, but need not, serve more than one function, such as a thickener, gellant, film-former, sensory enhancer, lubricant, emulsifier, stabilizer, suspending agent, moisturizer, spreading aid, carrier and the like for enhancing the efficacy, deposition or delivery of the antiperspirant agents and for improving the aesthetic properties of an antiperspirant composition in which they are included.

Generally, the amount of the cationic hydrophobically modified polymer employed in the antiperspirant compositions of the invention can vary in the range of from about 0.01 wt. % to about 20 wt. % (polymer solids), based on a total antiperspirant composition weight basis. In one aspect, when employed as polymeric gelling agents, the cationic hydrophobically modified polymer can be employed in a range from about 0.1 wt. % to about 15 wt. %, in another aspect from about 0.5 wt. % to about 10 wt. %, and in a further aspect from about 1 wt. % to about 3 wt. %, on a polymer solids basis based on the weight of the total antiperspirant composition.

Antiperspirant Agents

Various antiperspirant agents that can be utilized according to the present invention include conventional antiperspirant metal salts and complexes of metal salts. In one aspect of the invention the metal salts and metal salt complexes utilized as the antiperspirant agents are acidic and are based on aluminum and zirconium and combinations thereof. These salts include but are not limited to aluminum halides, aluminum hydroxyhalides, aluminum sulfate, zirconium (zirconyl) oxyhalides, zirconium (zirconyl)hydroxyhalides, and mixtures or complexes thereof. Complexes of aluminum and zirconium salts include aluminum and zirconium salt complexes with amino acids, such as, for example, glycine or complexes with a glycol, such as, for example, propylene glycol (PG) or polyethylene glycol (PEG). Exemplary antiperspirant agents include but are not limited to aluminum chloride, aluminum chlorohydrate, aluminum dichlorohydrate, aluminum sesquichlorohydrate, zirconyl hydroxychloride, aluminum chlorohydrex PEG (aluminum chlorohydrex polyethylene glycol), aluminum chlorohydrex PG (aluminum chlorohydrex propylene glycol), aluminum dichlorohydrex PEG (aluminum dichlorohydrex polyethylene glycol), aluminum dichlorohydrex PG (aluminum dichlorohydrex propylene glycol), aluminum sesquichlorohydrex PEG (aluminum sesquichlorohydrex polyethylene glycol), aluminum sesquichlorohydrex PG (aluminum sesquichlorohydrex propylene glycol), aluminum zirconium trichlorohyrate, aluminum zirconium tetrachlorohyrate, aluminum zirconium pentachlorohyrate, aluminum zirconium octachlorohyrate, aluminum zirconium chlorohydrex GLY (aluminum zirconium chlorohydrex glycine), aluminum zirconium trichlorohydrex GLY (aluminum zirconium trichlorohydrex glycine), aluminum zirconium tetrachlorohyrex GLY (aluminum zirconium tetrachlorohyrex glycine), aluminum zirconium pentachlorohyrex GLY (aluminum zirconium pentachlorohyrex glycine), and aluminum zirconium octachlorohyrex GLY (aluminum zirconium octachlorohyrex glycine). Other antiperspirant agents include ferric chloride and zirconium powder. Mixtures of any of the foregoing antiperspirant agents are also suitable for use in the present invention.

The amount of the antiperspirant agent incorporated into the antiperspirant compositions of the present invention is an amount that is sufficient to reduce the flow of perspiration from the location to which the antiperspirant product is applied, for example to the axillary area of the human body, while providing a suitably low pH to neutralize the cationic hydrophobically modified polymer to attain a desired viscosity. If the desired amount of antiperspirant agent loading is reached before the cationic hydrophobically modified polymer is sufficiently neutralized to achieve the desired viscosity profile, auxiliary acidification agents can be added to effect the desired viscosity profile.

Generally, the level of antiperspirant agent utilized in the compositions of the present invention range from about 0.5 wt. % to about 35 wt. % based on the total weight of the antiperspirant composition. In another aspect of the invention, the amount of antiperspirant agent in the composition can range from about 5 wt. % to about 25 wt. %, in a further aspect from about 5 wt. % to about 20 wt. %, and in a still further aspect from about 10 wt. % to about 15 wt. %, based on the total weight of the composition. The foregoing weight percentages are calculated on an anhydrous metal salt basis exclusive of the complexing agent (e.g., glycine or glycol).

Water

Water is utilized as a diluent in the antiperspirant compositions of the invention. In one aspect, the amount of water can range from about 10 wt. % to about 95 wt. % of the weight of the total antiperspirant composition. In another aspect the amount of water can range from about 15 wt. % to about 90 wt. %, from about 25 wt. % to about 85 wt. %, and in still further aspect from about 40 wt. % to about 75 wt. %, based on the total weight of the antiperspirant composition.

Monoalcohol

Optionally, the antiperspirant compositions of the present invention can include an auxiliary solvent/drying agent selected from at least one lower monoalcohol component. Suitable lower monoalcohols are selected from linear and branched $C_1$ to $C_5$ alkyl monoalcohols. Exemplary lower monoalcohols include methyl alcohol, ethyl alcohol, n-propyl alcohol, isopropyl alcohol, n-butyl alcohol, isobutyl alcohol, t-butyl alcohol, and amyl alcohol (all isomers). When present in the antiperspirant compositions of the invention, the lower monoalcohol(s) can be utilized in an amount ranging from about 0.1 wt. % to about 35 wt. % by weight of the total antiperspirant composition in one aspect, from about 0.5 wt. % to about 25 wt. % in another aspect, and from about 1 wt. % to about 20 wt. % in a further aspect.

Emollient

Optionally, the antiperspirant compositions of the present invention can include an emollient selected from silicone fluids (e.g., volatile silicone oils and non-volatile silicone oils); mineral oils; petrolatums; vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); and polyalkylene glycols; lanolin and lanolin derivatives; and the like. The emollient can be used alone or in combination with one or more emollients of the present invention. The emollient(s) can be utilized in an amount ranging from about 0.5 wt. % to about 30 wt. % by weight of the total antiperspirant composition in one aspect 0.1 wt. % to 25 wt. % in another aspect, and 5 wt. % to 20 wt. % is a further aspect.

Volatile silicone oils include cyclic and linear polydimethylsiloxanes, low molecular weight organo-functional silicones, and the like. Cyclic volatile silicones (cyclomethicones) typically contain about 3 to about 7 silicon atoms, alternating with oxygen atoms, in a cyclic ring structure. Each silicon atom is typically substituted with two alkyl groups, such as, for example, methyl groups. Volatile linear polydimethylsiloxanes (dimethicones) typically contain about 2 to about 9 silicon atoms, alternating with oxygen atoms in a linear arrangement. Each silicon atom is also substituted with two alkyl groups (the terminal silicon atoms are substituted with three alkyl groups), such as, for example, methyl groups. The linear volatile silicones typically have viscosities of less than about 5 cP at 25° C., while the cyclic volatile silicones typically have viscosities of less than about 10 cP at 25° C. "Volatile" means that the silicone has a measurable vapor pressure, or a vapor pressure of at least 2 mm of Hg at 20° C. Non-volatile silicones have a vapor pressure of less than 2 mm Hg at 20° C. A description of volatile silicones is found in Todd and Byers, "Volatile Silicone Fluids for Cosmetics", *Cosmetics and Toiletries*, Vol. 91(1), pp. 27-32 (1976), and in Kasprzak, "Volatile Silicones", *Soap/Cosmetics/Chemical Specialties*, pp. 40-43 (December 1986), each incorporated herein by reference.

Exemplary volatile cyclomethicones are D4 cyclomethicone (octamethylcyclotetrasiloxane), D5 cyclomethicone (decamethylcyclopentasiloxane), D6 cyclomethicone, and blends thereof (e.g., D4/D5 and D5/D6). Volatile cyclomethicones and cyclomethicone blends are commercially available from G.E. Silicones as SF1173, SF1202, SF1256, and SF1258, Dow Corning Corporation as Dow Corning® 244, 245, 246, 345, and 1401 Fluids. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning Corporation as Dow Corning 200® Fluid (e.g., product designations 0.65 CST, 1 CST, 1.5 CST, and 2 CST) and Dow Corning® 2-1184 Fluid.

Exemplary volatile low molecular weight organo-functional silicones include phenyl trimethicone, caprylyl trimethicone, caprylyl methicone, and hexyl methicone, and blends thereof. Low molecular weight organo-functional silicones are commercially available from Clariant under the trade name Silcare® 41M10, Slicare® 31M60, Silcare® 41M10, and Silcare® 41M15.

The non-volatile silicone oils useful as emollients in the present invention are linear and typically have viscosities of from about 10 cP to about 100,000 cP at 25° C. They typically contain above about 10 dialkyl/diaryl or monoalkyl/monoaryl substituted silicon atoms, alternating with oxygen atoms in a linear arrangement. They include polyalkylsiloxane, polyarylsiloxane, and polyalkylarylsiloxane polymers. Exemplary non-volatile silicone oils include the polydimethylsiloxanes (dimethicones), polydiethylsiloxanes, polymethylphenylsiloxanes, and the like. In one aspect of the invention, the non-volatile silicone oil is selected from a non-volatile polydimethylsiloxane having a viscosity range from about 10 cP to about 100,000 cP at 25° C. Non-volatile dimethicones are commercially available from Dow Corning Corporation as Dow Corning 200® Fluid (product designations 10 CST through 10,000 CST).

Mineral oils and petrolatums include cosmetic, USP and NF grades and are commercially available from Penreco under the Drakeol® and Penreco® trade names.

Exemplary vegetable oils suitable an emollient component in the present invention include but are not limited to peanut oil, sesame oil, avocado oil, coconut oil, cocoa butter, almond oil, safflower oil, corn oil, cotton seed oil, castor oil, olive oil, jojoba oil, palm oil, palm kernel oil, soybean oil, wheat germ oil, linseed oil, sunflower seed oil; and the mono-, di-, and triglycerides thereof. Exemplary mono-, di- and triglycerides are, for example, caprylic triglyceride, capric triglyceride, caprylic/capric triglyceride, and caprylic/capric/lauric triglyceride, caprylic/capric/stearic triglyceride, and caprylic/capric/linoleic triglyceride.

Ethoxylated mono- and diglycerides are also suitable as an emollient component of the present invention, such as, for example, PEG-8 Caprylic/Capric Glycerides.

Suitable fatty alcohol emollients include but are not limited to fatty alcohols containing 8 to 30 carbon atoms. Exemplary fatty alcohols include capryl alcohol, pelargonic alcohol, capric alcohol, lauryl alcohol, myristyl alcohol, cetyl alcohol, isocetyl alcohol, stearyl alchohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acid emollients include but are not limited to fatty acids containing 10 to 30 carbon atoms. Exemplary fatty acids are selected from capric acid, lauric acid, myristic acid, palmitic acid, stearic acid, oleic acid, linoleic acid, arachidic acid, behenic acid, and mixtures thereof.

Suitable fatty acid and fatty alcohol ester emollients include but are not limited to hexyl laurate, decyl oleate, isopropyl stearate, isopropyl isostearate, butyl stearate, octyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, lauryl lactate, diethyl hexyl maleate, PPG-14 butyl ether and PPG-2 myristyl ether propionate, cetearyl octanoate, and mixtures thereof.

Alkoxylated fatty alcohols are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect of the invention the ethoxylated fatty alcohols can be represented by the formula R—(OCH$_2$CH$_2$)$_n$—OH, wherein R represents the aliphatic residue of the parent fatty alcohol and n represents the number of molecules of ethylene oxide. In another aspect of the invention, R is derived from a fatty alcohol containing 8 to 30 carbon atoms. In one aspect n is an integer ranging from 2 to 50, 3 to 25 in another aspect, and 3 to 10 in a further aspect. In a still further aspect, R is derived from a fatty alcohol emollient set forth above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and mixed ethoxylated/propoxylated adducts of the foregoing fatty alcohols are also contemplated within the scope of the invention. The ethylene oxide and propylene oxide units of the ethoxylated/propoxylated fatty alcohols can be arranged in random or in blocky order.

More specific examples of ethoxylated alcohols are but are not limited to Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 pareth 3-8, C11-15 pareth 5-40, C11-21 Pareth 3-10, C12-13 pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, Trideceth 2-10, and so on.

Specific examples of propoxylated alcohols are but are not limited to PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols are but are not limited to PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 C9-15 Pareth-6, PPG-6 C9-11 Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Alkoxylated fatty acids are formed when a fatty acid is reacted with an alkylene oxide or with a pre-formed polymeric ether. The resulting product may be a monoester, diester, or mixture thereof. Suitable ethoxylated fatty acid ester emollients suitable for use in the present invention are products of the addition of ethylene oxide to fatty acids. The product is a polyethylene oxide ester of a fatty acid. In one aspect of the invention, the ethoxylated fatty acid esters can be represented by the formula $R-C(O)O(CH_2CH_2O)_n-H$, wherein R represents the aliphatic residue of a fatty acid and n represents the number of molecules of ethylene oxide. In another aspect, n is an integer ranging from 2 to 50, 3 to 25 in another aspect, and 3 to 10 in a further aspect. In still another aspect of the invention, R is derived from a fatty acid containing 8 to 24 carbon atoms. In a still further aspect, R is derived from a fatty acid emollient set forth above. It is to be recognized that propoxylated and ethoxylated/propoxylated products of the foregoing fatty acids are also contemplated within the scope of the invention. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Benzoate ester emollients are selected from but not limited to $C_{12}$-$C_{15}$ alkyl benzoate, isostearyl benzoate, octyl dodecyl benzoate, stearyl benzoate, dipropylene glycol dibenzoate, methyl gluceth-20 benzoate, castor oil benzoate, cetyl ricinoleate benzoate, ethylhexyl hydroxystearate benzoate, dimethicone PEG/PPG-20/23 benzoate, and dimethicone PEG-8 benzoate.

Guerbet ester emollients are formed from the esterification reaction of a Guerbet alcohol with a carboxylic acid. Guerbet ester emollients are commercially available from the Noveon Consumer Specialties Divisions of Lubrizol Advanced Materials, Inc. under product designations G-20, G-36, G-38, and G-66.

Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from the Noveon Consumer Specialties Division of Lubrizol Advance Materials, Inc. under the trade names Lanolin LP 108 USP, Lanolin USP AAA, Acetulan™, Ceralan™, Lanocerin™, Lanogel™ (product designations 21 and 41), Lanogene™, Modulan™, Ohlan™, Solulan™ (product designations 16, 75, L-575, 98, and C-24), Vilvanolin™ (product designations C, CAB, L-101, and P).

Humectant

Optionally, the antiperspirant compositions of the present invention can include a humectant selected from polyhydric alcohols; allantoin; pyrrolidone carboxylic acid and its salts; hyaluronic acid and its salts; sorbic acid and its salts; urea; lysine, arginine, cystine, guanidine, and other amino acids; glycolic acid and glycolate salts (e.g. ammonium salts and quaternary alkyl ammonium salts); lactic acid and lactate salts (e.g. ammonium salts and quaternary alkyl ammonium salts); sugars and starches, and sugar and starch derivatives (e.g. alkoxylated glucose derivatives); D-panthenol; lactamide monoethanolamine; acetamide monoethanolamine; and the like; and mixtures thereof. The humectant component can be present in an amount ranging from about 0.1 wt. % to about 15 wt. % in one aspect, from about 1 wt. % to about 10 wt. % in another aspect, and from 3 wt. % to about 8 wt. % in a further aspect, based on the weight of the total antiperspirant composition.

The Alkoxylated glucose derivatives include alkoxylated methyl glucosides such as ethoxylated and propoxylated methyl glucose ethers. The number of alkylene oxide groups in the polyether groups can range from about 2 and above in one aspect to about 5 to 50 in another aspect. Representative examples of alkoxylated methyl glucosides include Methyl Gluceth-10, Methyl Gluceth-20, and PPG-10 Methyl Glucose Ether, available from the Noveon Consumer Specialties Division of Lubrizol Advance Materials, Inc. under the Glucam® trade name (e.g., product designations E-10, E-20, P-10, and P-20).

Exemplary polyhydric alcohols include but are not limited to glycerin, glycols such as, for example diethylene glycol, triethylene glycol, 1,2-propylene glycol, 1,3-propylene glycol, dipropylene glycol, and tripropylene glycol, tetrapropylene glycol, butylene glycol, 1,3-butylene glycol, 2-methyl, 1,3-propanediol, 2,4-dihydroxy-2-methylpentane; hexanetriol; alditols such as, for example, sorbitol, mannitol and xylitol; dimethicone copolyols; and the like; and mixtures thereof.

Emulsifier

Optionally, the antiperspirant compositions of the present invention can include an emulsifier. The emulsifier can be selected from a water-in-oil emulsifier, an oil-in-water emulsifier, and mixtures thereof. In one aspect of the invention the emulsifier can be present in an amount ranging from about 0.5 wt. % to about 12 wt. %, from about 1 wt. % to about 15 wt. % in another aspect, and from about 5 wt. % to about 10 wt. % in a further aspect, based on the total weight of the antiperspirant composition.

Exemplary emulsifiers include but are not limited to $C_{12}$-$C_{18}$ fatty alcohols; alkoxylated $C_{12}$-$C_{18}$ fatty alcohols; $C_{12}$-$C_{18}$ fatty acids; and alkoxylated $C_{12}$-$C_{18}$ fatty acids, the alkoxylates each having 10 to 30 units of ethylene oxide, propylene oxide, and combinations of ethylene oxide/propylene oxide; $C_8$-$C_{22}$ alkyl mono- and oligoglycosides; ethoxylated sterols; partial esters of polyglycerols; esters and partial esters of polyols having 2 to 6 carbon atoms and saturated and unsaturated fatty acids having 12 to 30 carbon atoms; partial esters of polyglycerols; and organosiloxanes; and combinations thereof.

The fatty alcohols, acids and alkoxylated fatty alcohols and fatty acids are as described in the emollient description above. In one aspect of the invention the fatty alcohols and fatty acids each are ethoxylated with 10 to 30 units of ethylene oxide.

The $C_8$-$C_{22}$ alkyl mono- and oligoglycoside emulsifiers are prepared by reacting glucose or an oligosaccharide with primary fatty alcohols having 8 to 22 carbon atoms. Products which are obtainable under the trademark Plantacare® comprise a glucosidically bonded $C_8$-$C_{16}$ alkyl group on an oligoglucoside residue whose average degree of oligomerization is 1 to 2. Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Exemplary ethoxylated sterols include ethoxylated vegetable oil sterols such as, for example, soya sterols. The degree of ethoxylation is greater than about 5 in one aspect, and at least about 10 in another aspect. Suitable ethoxylated sterols are PEG-10 Soy Sterol, PEG-16 Soy Sterol and PEG-25 Soy Sterol.

The partial esters of polyglycerols have 2 to 10 glycerol units and are esterified with 1 to 4 saturated or unsaturated, linear or branched, optionally hydroxylated $C_8$-$C_{30}$ fatty acid residues. Representative partial esters of polyglycerols include diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

The saturated $C_{12}$-$C_{30}$ fatty alcohol emulsifiers are as described in the emollient description set forth above. In one aspect of the invention, the fatty alcohol emulsifier is selected from but not limited to cetyl alcohol, stearyl alcohol, arachidyl alcohol, behenyl alcohol and lanolin alcohol or mixtures of these alcohols, and as are obtainable in the hydrogenation of unsaturated vegetable oil and animal fatty acids.

Emulsifiers based on the esters and partial esters of polyols having 2 to 6 carbon atoms and linear saturated and unsaturated fatty acids having 12 to 30 carbon atoms are, for example, the monoesters and diesters of glycerol or ethylene glycol or the monoesters of propylene glycol with saturated and unsaturated $C_{12}$ to $C_{30}$ fatty acids.

The partially esterified polyglycerol emulsifiers include 2 to about 10 glycerol units and esterified with 1 to 5 saturated or unsaturated, linear or branched, optionally hydroxylated $C_8$ to $C_{30}$ fatty acid residues. The organosiloxane emulsifiers are polymeric emulsifiers that contain at least one hydrophobic portion and at least one hydrophilic portion. The polymer backbone contains repeating siloxy units that can have cyclic, linear or branched repeating units, e.g. di(lower)alkylsiloxy units, typically dimethylsiloxy units.

The hydrophilic portion of the organosiloxane is generally achieved by substitution onto the polymeric backbone of a residue that confers hydrophilic properties to a portion of the molecule. The hydrophilic residue may be substituted on a terminus of the polymeric organosiloxane, or on any one or more repeating units of the polymer. Generally, the hydrophilic residue is derived from ethylene oxide units that are grafted onto the polymer backbone. In general, the repeating dimethylsiloxy units of modified polydimethylsiloxane emulsifiers are hydrophobic in nature due to the methyl groups, and confer the hydrophobicity properties to the molecule. In addition, longer chain alkyl residues, hydroxy terminated polypropyleneoxy residues, hydroxy terminated polyether residues comprising a combination of ethylene oxide and propylene oxide residues, and/or other types of residues can be substituted onto the siloxy backbone to confer additional emulsification properties to the backbone. Polyether substituted organosiloxane emulsifiers are known as dimethicone copolyols and are widely commercially available. The dimethicone polyols can be random or block copolymers. A generally useful class of dimethicone polyols is block copolymers having blocks of polydimethylsiloxane and blocks of polyalkylene oxide, such as blocks of polyethylene oxide, polypropylene oxide, or both.

Dimethicone copolyols are disclosed in U.S. Pat. Nos. 5,136,063 and 5,180,843, the disclosures of which are incorporated herein by reference. In addition, dimethicone copolyols are commercially available under the Silsoft® and Silwet® brand names from the General Electric Company (GE-OSi). Specific product designations include but are not limited to Silsoft 305, 430, 475, 810, 895, Silwet L 7604 (GE-OSi); Dow Corning® 5103 and 5329 from Dow Corning Corporation; and Abile dimethicone copolyols, such as, for example WE 09, WS 08, EM 90 and EM 97 from Degussa Goldschmidt Corporation; and Silsense™ dimethicone copolyols, such as Silsense Copolyol-1 and Silsense Copolyol-7, sold by Noveon, Inc.

Blends of dimethicone copolyols in cyclomethicone fluids are also useful emulsifiers in the present invention. An exemplary dimethicone/cyclomethicone blend is commercially available as Dow Corning® 5225 C and is a 10 wt. % dispersion of PEG/PPG-18/18 Dimethicone in cyclopentasiloxane fluid available from Dow Corning Corporation.

Auxiliary Gelling Agents

The antiperspirant compositions of the invention can contain an optional auxiliary gelling agent (or thickener) selected from cellulose ethers such as, for example, methyl cellulose (MC), hydroxypropyl methylcellulose (HPMC), hydroxyethyl cellulose (HEC), and hydroxypropylcellulose (HPC); modified cellulose ethers, such as, for example MC, HPMC, HEC, and HPC that is modified with a $C_{12}$-$C_{24}$ alkyl group through an ether linkage on the cellulosic backbone; carrageenan; polyvinylpyrrolidone; Polyquaternium-4, Polyquaternium-10; fatty acid esters of alkoxylated pentaerythritol, such as, for example, PEG-150 pentaerythriyl tetrastearate; fatty acid esters of alkoxylated methyl glucoside, such as, for example, PEG-120 methyl glucose dioleate and PEG-120 methyl glucose trioleate available from Noveon, Inc under the trade names, Glucamate® DOE-120 and Glucamate LT, respectively. Hydrophobically modified non-ionic urethane thickeners, such as, for example, polymers marketed under the trade name Aculyn® 44 from Rohm & Haas, are also useful. The auxiliary gelling agents can be present in an amount ranging from 0.1 wt. % to about 5 wt. % of the total weight of the antiperspirant composition.

Auxiliary Acidification Agents

Optionally, auxiliary acidification agents can be added in combination with the acidic antiperspirant agent to neutralize the cationic hydrophobically modified polymer so that a desired viscosity can be obtained. The auxiliary acidification agents can be selected from organic acids, including amino acids, inorganic mineral acids, and mixtures thereof. Non-limiting examples of acidic auxiliary acidification agents include acetic acid, citric acid, fumaric acid, glutamic acid, glycolic acid, hydrochloric acid, lactic acid, nitric acid, phosphoric acid, sodium bisulfate, sulfuric acid, tartaric acid, and the like, and mixtures thereof. The auxiliary acidification agent can be utilized in any amount necessary to obtain a desired acidic pH value when formulating the antiperspirant composition. Typically, the pH value can be less than 7.

pH Adjusting Agent

An optional pH adjusting agent can be added either to a previously acid-swollen or water-swollen cationic hydrophobically modified polymer or to a formulation containing a cationic hydrophobically modified polymer. Thus, the pH adjusting agent can be utilized in any amount necessary to obtain a desired pH value in the final antiperspirant composition. Non-limiting examples of alkaline pH adjusting agents include alkali metal hydroxides, such as sodium hydroxide, and potassium hydroxide; ammonium hydroxide; organic bases, such as triethanolamine, diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine; and alkali metal salts of inorganic acids, such as sodium borate (borax), sodium phosphate, sodium pyrophosphate, and the like, and mixtures thereof.

Preservatives

If desired optional preservative agents can be utilized in the antiperspirant composition. Exemplary preservatives include polymethoxy bicyclic oxazolidine, methyl paraben, propyl paraben, ethyl paraben, butyl paraben, benzoic acid and the salts of benzoic acid, e.g., sodium benzoate, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, sorbic acid, salicylic acid salts, and the like, and mixtures thereof. Such suitable preservatives typically comprise about 0.01 wt. % to about 1.5 wt. %, preferably about 0.1 wt. % to about 1 wt. %, and more preferably about 0.3 wt. % to about 1 wt. % of the total weight of the personal care compositions of the present invention.

Deodorant/Antimicrobial Actives

Optionally, one or more deodorant and antimicrobial actives can be incorporated into the antiperspirant compositions of the invention. Examples of suitable deodorant actives include 2-amino-2-methyl-1-propanol (AMP), ammonium phenolsulfonate; benzalkonium chloride; benzethonium chloride, bromochlorophene, cetyltrimethylammonium bromide, cetyl pyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarban, triclosan, zinc phenolsulfonate, zinc ricinoleate, and mixtures thereof. The deodorant/antimicrobial component can range of from about 0.1 wt. % to about 5 wt. % of total antiperspirant composition.

Chelating Agents

When utilized, suitable chelating agents include EDTA (ethylene diamine tetraacetic acid) and salts thereof such as disodium EDTA, citric acid and salts thereof, cyclodextrins, and the like, and mixtures thereof. Such suitable chelators typically comprise about 0.001 wt. % to about 3 wt. %, preferably about 0.01 wt. % to about 2 wt. %, and more preferably about 0.01 wt. % to about 1 wt. % of the total weight of the personal care compositions of the present invention.

Botanical Actives

Optionally, the antiperspirant compositions of the invention can contain botanical active material extracts. Extracted botanical active materials can include any water soluble or oil soluble material extracted from a particular plant, fruit, nut, or seed. In one aspect of the invention the antiperspirant compositions the botanical actives are present in an amount ranging from about 0.1 wt. % to about 10 wt. %, from about 0.5 wt. % to about 8 wt. percent in another aspect, and from about 1 wt. % to about 5 wt. % in a further aspect, of the total antiperspirant composition.

Suitable botanical actives can include, for example, extracts from Echinacea (e.g., sp. angustifolia, purpurea, pallida), yucca glauca, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel. Botanical extracts include, for example, chlorogenic acid, glutathione, glycrrhizin, neohesperidin, quercetin, rutin, morin, myricetin, absinthe, and chamomile.

Bead Components

Optionally, the antiperspirant composition can contain from about 0.1 wt. % to about 10 wt. % based on the total weight of the composition of a cosmetic bead component suspended in the antiperspirant. Cosmetic beads can be included for aesthetic appearance or can function as micro- and macroencapsulants in the delivery of beneficial agents to the skin. Exemplary bead components include but are not limited to microsponges, gelatin beads; alginate beads; expanded polystyrene beads; jojoba beads; polyethylene beads; Unispheres® cosmetic beads (Induchem), such as for example, product designations YE-501 and UEA-509; Lipopearls™ vitamin E encapsulated in gelatin beads (Lipo Technologies Inc.); and Confetti™ (United Guardian Company).

Other Additives

Other optional formulation additives can be included in the antiperspirant compositions described herein. Other additives typically can include, but are not limited to surfactants (as emulsifying agents, foam boosters, solubilizing agents, and suspending agents); suspending agents; antifoaming agents; film-formers; skin protectants; binders; antifungal agents; absorbents; opacifying agents; pearlizing agents; colorants; pigments; antioxidants, propellants, spreading aids, physiologically active agents, astringents, vitamins, fragrance and fragrance solubilizers; titanium dioxide; calcium carbonate; talc; teatree powder; potato starch; tapioca starch; paraffin; kaolin clay; zinc oxide; talc; beeswax; zeolites; silica; and the like; and combinations thereof.

While overlapping weight ranges for the various components that make up the antiperspirant compositions of the invention have been expressed for selected embodiments and aspects of the invention, it should be readily apparent that the specific amount of each component in the antiperspirant composition will be selected from its disclosed range such that the amount of each component is adjusted so that the sum of all components in the composition will total 100 weight percent. The amounts employed will vary with the purpose and character of the desired product and can be readily determined by one skilled in the formulation arts and from the literature.

The choice and amount of ingredients in formulated antiperspirant compositions containing the cationic hydrophobically modified polymer will vary depending on the product and its function, as is well known to those skilled in the formulation arts. An extensive listing of substances and their conventional functions and product categories appears in the INCI Dictionary, generally, and in Vol. 2, Sections 4 and 5 of the Seventh Edition, in particular, incorporated herein by reference.

As disclosed herein the antiperspirant compositions containing the polymers of the present invention can contain various conventional additives and adjuvants known in the art, some of which can serve more than one function. For example, a particular component can be listed herein as an emollient but can also function as an emulsifier, humectant, solubilizing agent, and the like.

Antiperspirant compositions containing a cationic associative polymer can be packaged and dispensed from containers, such as jars, bottles, tubes, spray bottles, wipes, cans, roll-on containers, stick containers, and the like, without limitation.

The following examples further describe and demonstrate embodiments within the scope of the present invention. These examples are presented solely for the purpose of illustration, and are not to be construed as limitations of the present invention since many variations thereof are possible without departing from the spirit and scope thereof. Unless otherwise specified weight percents (wt. %) are given in wt. % based on the weight of the total composition.

Materials

The materials are generally commercially available from chemical supply houses known to those skilled in the chemical arts or from the supplier indicated below.

| | |
|---|---|
| AMHEC | Allyl modified hydroxyethyl cellulose powder (<180 μm)(TYLOSE ® AM H40 YP2; Clariant Corp.) |
| AZG-368 | Aluminum Zirconium Tetrachlorohydrex Glycine Complex (Summit Research Labs) |
| AZG-442 | Aluminum Zirconium Chlorohydrex Glycine Complex (Summit Research Labs) |
| Arlamol E | PPG-15 Stearyl Ether (Uniquema) |
| Arlasolve ™ 200 | isoceteth-20 ethoxylated fatty alcohol (Uniquema) |
| BEM25 | Beheneth-25 methacrylate |
| Brij ® 72 | Steareth-2 (Uniquema) |
| Brij ® 721 | Steareth-21 (Uniquema) |
| C897 | Ethoxylated octylphenol, INCI Name Octoxynol-40, HLB of about 18 (Igepal ® CA-897, Rhodia, Inc.) |
| Crothix ™ Liquid | PEG-150 Pentaerythrityl Tetrastearate (Croda Inc) |
| CSEM25 | Ceteareth-25 methacrylate |
| DMAEMA | 2-(N,N-dimethylamino)ethyl methacrylate |
| DMAPMAm | 2-(N,N-dimethylamino)propyl methacrylamide |
| Dow Corning ® 200 (50 CST) | Polydimethyl siloxane fluid (Dow Corning Corporation) |
| Dow Corning ® 345 | Cyclopentasiloxane (and) Cyclohexasiloxane (Dow Corning Corporation) |
| Dow Corning ® 5225 C | Cyclopentasiloxane (and) PEG/PPG-18/18 Dimethicone (Dow Corning Corporation) |
| E407 | Secondary $C_{11}$ ethoxylate having 40 ethylene oxide units per alcohol unit (EMULSOGEN ® EPN 407, Clariant Corp.) |

-continued

| | |
|---|---|
| EA | Ethyl acrylate |
| Glucam ® P-10 | PPG-10 Methyl Glucose Ether (Noveon, Inc.) |
| Glucamate ® LT | PEG-120 Methyl Glucose Trioleate (and) Propylene Glycol (and) Water (Noveon, Inc. |
| Glydant Plus ® | blend of 1,3-dimethylol-5,5-dimethyl hydantoin and iodopropynyl butylcarbamate (Lonza Group Ltd.) |
| HEMA | 2-Hydroxyethyl methacrylate |
| Lanette ® 18 | stearyl alcohol (Cognis Corp.) |
| L.A.S. | PEG-8 Caprylic/Capric Glycerides (Gattefosse S. A.) |

Following the addition of the monomer components to the reactor vessel components, the resulting mixture is agitated (about 200 rpm) at a temperature range of about 30 to about 40° C. under a nitrogen atmosphere until an emulsion is formed. A solution of about 0.15 parts by wt. of sodium persulfate in about 3 parts of water is added to the monomer emulsion with under agitation to initiate the polymer reaction. The reaction mixture is maintained at a temperature range of about 600 to 62° C. for about 2.5 hours after the initiator is added. Additional quantities of initiator are added at about 0.5 hours and about 1.5 hours after the reaction is first initiated (about 0.2 parts by wt. of sodium persulfate in about 3.5 parts of water in each instance).

TABLE 1

| Ex. No. | Pol. No. | ASV Mon. (%) | HNV Mon. (%) | AV Mon. (%) | SVS Mon. (%) | Other Mon. (%) | Surfactant (%) |
|---|---|---|---|---|---|---|---|
| 1 | X | DMAEMA (35) | EA (55.9) | BEM25 (3) | RAL307 (4) | TEGDMA (0.1) HEMA (2) | E407 (7) |
| 2 | y | DMAEMA (35) | EA (55.9) | BEM25 (3) | RAL307 (4) | TEGDMA (0.1) HEMA (2) | E407 (5.5) |
| 3 | AC | DMAEMA (30) DMAPMAm (5) | EA (55.9) | BEM25 (3) | RAL307 (4) | TEGDMA (0.1); HEMA (2) | E-407 (5.5) |
| 4 | AF | DMAEMA (35) | EA (55.9) | CSEM25 (3) | R307 (4) | TEGDMA (0.1); HEMA (2) | P-38 (7) |
| 5 | AG | DMAEMA (35) | EA (56.4) | CSEM25 (1) BEM25 (1.5) | R307 (4) | TEGDMA (0.1); HEMA (2) | P-38 (7) |
| 6 | AH | DMAEMA (35) | EA (55.9) | BEM25 (3) | RAL307 (4) | TEGDMA (0.1); HEMA (2) | P-38 (7) |
| 7 | AI | DEAEMA (35) | EA (55.9) | BEM25 (3) | RAL307 (4) | TEGDMA (0.1); HEMA (2) | E-407 (5.5) |
| 8 | AW | DMAEMA (35) | EA (55.9) | CSEM (3.0) | RAL307 (4) | TEGDMA (0.1); HEMA (2) | E-407 (5.5); AMHEC (0.1) |

-continued

| | |
|---|---|
| Locron L | Aluminum Chlorhydrate |
| P-38 | Ethoxylated (27) cetearyl alcohol, INCI name Ceteareth-27, reportedly having an HLB of 19 (PLURAFAC ® A-38, BASF Corp.) |
| PQ-4 | Polyquaternium-4 |
| PQ-10 | Polyquaternium-10 |
| R307 | A randomly ethoxylated/propoxylated 1,4-butanediol vinyl ether having the empirical formula $CH_2=CHO(CH_2)_4O(C_3H_6O)_4(C_2H_4O)_{30}H$ (EMULSOGEN ® R307, Clariant Corporation) |
| RAL307 | A randomly ethoxylated/propoxylated allyl ether having the empirical formula $CH_2=CHCH_2O(C_3H_6O)_4(C_2H_4O)_{30}H$; (EMULSOGEN ® RAL307, Clariant Corporation) |
| TEGDMA | Triethyleneglycol dimethacrylate |
| Unispheres ® | cosmetic beads containing lactose and cellulose (and) hydroxypropyl methylcellulose (and) chlorophyllin-copper (Induchem AG) |

EXAMPLES 1 to 8

Cationic hydrophobically modified polymer gellants of the invention are prepared by weighing the amounts of monomer set forth in Table 1 into an agitator equipped reactor vessel containing about 350 parts by wt. of deionized water; the surfactant amounts set forth in Table 1, and about 0.3 parts by wt. of sodium lauryl sulfate (30% active) anionic surfactant. All monomer % values in the Table I are given in wt. % based on total monomer mixture weight; whereas all surfactant % values are based on total emulsion weight (i.e., combined weight of all monomers, additives, surfactants, and water).

The resulting polymer emulsions are cooled to a temperature in the range of about 44° to about 46° C. over a period of about 45 minutes and an oxidizing solution is added to the reaction mixture in two portions at one hour intervals thereafter. Each oxidizing (redox) solution contained about 0.15 parts by wt. of t-butylhydroperoxide (70% active), about 0.015 parts by wt. of sodium lauryl sulfate (30% active) and about 0.15 parts by wt. of sodium metabisulfite in about nine parts by wt. of water.

The polymer emulsions are then cooled to ambient room temperature and discharged from the reactor, bottled, and stored under an inert atmosphere at ambient room temperature. The emulsions are analyzed to determine the pH, percent total solids based on polymer content, Brookfield viscosity (spindle #2, 20 rpm @ ambient room temperature) and particle size (nm). The unneutralized product polymer emulsions generally have a pH in the range of about pH 7.5 to about 9; total solids in the range of about 15 to about 25 weight percent; a Brookfield viscosity in the range of about 10 to about 100 mPa·s, and an average particle size in the range of about 80 nm to about 260 nm.

The polymer emulsions of the cationic hydrophobically modified polymers shown in Table I, are stable, based on studies of up to 5 freeze/thaw (F/T) cycles, and shelf storage at ambient room temperature for at least about 5 months. The viscosity of the foregoing cationic hydrophobically modified polymer emulsions that are stored for at least about 5 weeks at a temperature of about 45° C. remains stable, any viscosity increase being not more than about 100 mPa·s.

EXAMPLE 9

This example illustrates the use a cationic hydrophobically modified polymer gellant prepared according to the method of Example 8 in a clear roll-on antiperspirant composition of the invention shown in Table 2 below.

TABLE 2

| | Ingredient | wt. % |
|---|---|---|
| | Part A | |
| 1 | Deionized (D.I.) Water | 27.6 |
| 2 | Butylene Glycol (humectant) | 3.0 |
| 3 | Glycerin (humectant) | 3.0 |
| 4 | Locron L (antiperspirant agent 50% solution) | 36.0 |
| | Part B | |
| 5 | D.I. Water | 10.0 |
| 6 | Polymer of Ex. 8 (20 wt. % polymer solids) (gellant) | 15.0 |
| | Part C | |
| 7 | Arlasolve ™ 200 (solubilizing agent) | 5.0 |
| | Part D | |
| 8 | Glydant Plus ® (preservative) | 0.40 |

The Part A and Part B components are separately formulated by uniformly the ingredients set forth in the table above. Part A is added to Part B and homogeneously mixed. Part C is added to the Part A+B mixture, followed by addition of Part D to the Part A+B+C mixture. The components are mixed to obtain a clear roll-on formulation.

EXAMPLE 10

A clear antiperspirant gel formulation is made with the ingredients set forth in Table 3 below.

TABLE 3

| | Ingredient | wt. % |
|---|---|---|
| | Part A | |
| 1 | Deionized (D.I.) Water | 9.6 |
| 2 | Butylene Glycol (humectant) | 5.0 |
| 3 | Glycerin (humectant) | 10.0 |
| 4 | L.A.S. (emollient) | 2.0 |
| 5 | Locron L (antiperspirant agent 50% solution) | 36.0 |
| | Part B | |
| 6 | D.I. Water | 10.0 |
| 7 | Polymer of Ex. 8 (20 wt. % polymer solids) (gellant) | 25.0 |
| | Part C | |
| 8 | Denatured Ethanol (solvent) | 2.0 |
| | Part D | |
| 9 | Glydant Plus ® (preservative) | 0.4 |

The ingredients of Part A and Part B are added to separate containers and mixed. The Part A and Part B components are combined and mixed. Parts C and D are sequentially added to the Part A+B component mixture and mixed to obtain a clear antiperspirant gel composition.

EXAMPLE 11

This example illustrates a clear antiperspirant formulation containing a bead component made with the ingredients set forth in Table 4 below.

TABLE 4

| | Ingredient | wt. % |
|---|---|---|
| | Part A | |
| 1 | Deionized (D.I.) Water | 17.1 |
| 2 | Butylene Glycol (humectant) | 3.0 |
| 3 | Glycerin (humectant) | 3.0 |
| 4 | Locron L (antiperspirant agent 50% solution) | 36.0 |
| | Part B | |
| 5 | D.I. Water | 10.0 |
| 6 | Polymer of Ex. 8 (20 wt. % polymer solids) (gellant) | 25.0 |
| | Part C | |
| 7 | Arlasolve ™ 200 (solubilizin agent) | 5.0 |
| | Part D | |
| 8 | Glydant Plus ® (preservative) | 0.40 |
| | Part E | |
| 9 | Unispheres ® (cosmetic beads) | 0.5 |

Part A and Part B are separately formulated by uniformly mixing the ingredients set forth in the table above. Part A is added to Part B and mixed. Part C is added to the Part A+B mixture, followed by the addition of Part D to the Part A+B+C mixture. The Part E bead component is added to the Part A+B+C+D mixture and mixed to obtain a clear antiperspirant gel formulation.

EXAMPLE 12

This example demonstrates the formulation of a roll-on antiperspirant emulsion composition. The ingredients listed in Table 5 below are formulated as follows. Disodium EDTA is mixed with D.I. water. Butylene glycol and the antiperspirant agent are then sequentially added to the EDTA/water mixture and mixed to form the Part A component. In a separate container the ingredients of the Part B component are added and mixed. The Part B components is added to the Part A component and mixed. The A+B component is heated to about 75° C. To a separate container the ingredients of Part C are added, mixed and heated to 75° C. The heated Part C component is mixed with the Part A+B component the temperature of which is maintained at 75° C. The A+B+C component is allowed to cool to about 40° C. to which the Part D component is added and mixed to obtain the roll-on emulsion product.

TABLE 5

| | Ingredient | wt. % |
|---|---|---|
| | Part A | |
| 1 | Deionized (D.I.) Water | 30.0 |
| 2 | Disodium EDTA (chelating agent) | 0.2 |
| 3 | Butylene glycol (humectant) | 5.0 |
| 4 | Locron L (antiperspirant agent 50% solution) | 36.0 |

TABLE 5-continued

| | Ingredient | wt. % |
|---|---|---|
| | Part B | |
| 5 | D.I. Water | 5.0 |
| 6 | Polymer of Ex. 8 (20 wt. % polymer solids) (gellant) | 5.0 |
| | Part C | |
| 7 | Lanette ® 18 (co-emulsifier) | 0.5 |
| 8 | Brij ® 72 (emulsifier) | 3.6 |
| 9 | Brij ® 721 (emulsifier) | 2.3 |
| 10 | Arlamol E (emollient) | 12.0 |
| | Part D | |
| 11 | Glydant Plus ® (preservative) | 0.40 |

EXAMPLE 13

This example illustrates the formulation of a clear roll-on antiperspirant from the ingredients set forth in Table 6.

TABLE 6

| | Ingredient | wt. % |
|---|---|---|
| | Part A | |
| 1 | Locron L (antiperspirant agent 50% solution) | 50.0 |
| | Part B | |
| 2 | Deionized (D.I.) Water | 5.0 |
| 3 | Polymer of Ex. 8 (20 wt. % polymer solids) (gellant) | 15.0 |
| | Part C | |
| 4 | Denatured Ethanol (solvent) | 30.0 |

The ingredients of Part B are mixed and added to Part A. Part C is added with mixing to obtain the roll-on product.

EXAMPLE 14

An antiperspirant composition containing the ingredients set forth in Table 7. The Part A component is formulated by adding the polyquaternium ingredients to warm D.I. water (approx. 45° C.). The remaining Part A ingredients are added and mixed. The Part B component is added to Part A. The ingredients of Part C are added together in a separate container and mixed. Part C is added to the Part A+B component and mixed. Part D and Part E are sequentially added to the Part A+B+C composition and mixed to give the antiperspirant product.

TABLE 7

| | Ingredient | wt. % |
|---|---|---|
| | Part A | |
| 1 | Deionized (D.I.) Water | 30.0 |
| 2 | Propylene Glycol (humectant) | 2.0 |
| 3 | PQ-4 (auxiliary gellant/conditioner) | 2.0 |
| 4 | Butylene Glycol (humectant) | 2.0 |
| | Part B | |
| 5 | AZG-442 (antiperspirant agent 35% solution) | 42.0 |
| | Part C | |
| 6 | Polymer of Ex. 8 (20 wt. % polymer solids) (gellant) | 10.0 |
| 7 | Deionized (D.I.) Water | 10.0 |

TABLE 7-continued

| | Ingredient | wt. % |
|---|---|---|
| | Part D | |
| 8 | Glydant Plus ® (preservative) | 0.3 |
| | Part E | |
| 9 | Denatured Ethanol (solvent) | 1.7 |

EXAMPLE 15

An antiperspirant composition is formulated from the ingredients in Table 8.

TABLE 8

| | Ingredient | wt. % |
|---|---|---|
| | Part A | |
| 1 | Deionized (D.I.) Water | 16.5 |
| 2 | PQ-10 (auxiliary gellant/conditioner) | 1.5 |
| 3 | Glucam ® P-10 (humectant) | 3.0 |
| 4 | Glucamate ® LT (auxiliary gellant) | 3.5 |
| 5 | Crothix ™ liquid (45% active) (auxiliary thickener) | 2.0 |
| 6 | Butylene Glycol (humectant) | 1.5 |
| | Part B | |
| 7 | AZG-442 (antiperspirant agent 35% solution) | 42.0 |
| | Part C | |
| 8 | Polymer of Ex. 8 (20 wt. % polymer solids) (gellant) | 10.0 |
| 9 | Deionized (D.I.) Water | 20.0 |

The Part A ingredients are mixed with moderate agitation. The Part B and Part C ingredients are sequentially added to the Part A component and mixed to obtain a homogeneous mixture to obtain the antiperspirant composition.

EXAMPLES 16 and 17

These examples are formulated from the ingredients set forth in Table 9.

TABLE 9

| | Ingredient | Ex. 16 wt. % | Ex. 17 wt. % |
|---|---|---|---|
| | Part A | | |
| 1 | Dow Corning ® 345 (emollient) | 8.0 | 8.0 |
| 2 | Dow Corning ® 200, 50 cst (emollient) | 2.0 | 2.0 |
| 3 | Dow Corning ® 5225 C (emulsifier) | 8.0 | 8.0 |
| | Part B | | |
| 4 | Deionized (D.I.) Water | 12.0 | 12.0 |
| 5 | Propylene Glycol (humectant) | 2.0 | 0 |
| 6 | Butylene Glycol (humectant) | 3.0 | 8.0 |
| 7 | Dipropylene glycol (humectant) | 3.0 | 0 |
| 8 | AZG-442 (antiperspirant agent 35% solution) | 50.0 | 50.0 |
| | Part C | | |
| 9 | Polymer of Ex. 8 (20 wt. % polymer solids) (gellant) | 5.0 | 5.0 |
| 10 | Deionized (D.I.) Water | 7.0 | 5.0 |
| 11 | Butylene Glycol (humectant) | 0 | 2.0 |

For each example, the Part A ingredients are mixed in a separate container to obtain a homogeneous mixture. The ingredients listed for Part B are mixed together in a separate container until homogeneous and slowly added to the Part A mixture under increasing agitation for 5 minutes or until the desired viscosity is attained. In a separate container the Part C components are mixed and then neutralized with 50% glycolic acid solution to a pH value of 5.0-5.5. Part C is added to the Part A+B mixture to obtain the final antiperspirant formulation.

EXAMPLE 18

This example is formulated as set forth in Examples 16 and 17 from the ingredients set forth in Table 10.

TABLE 10

| | Ingredient | wt. % |
|---|---|---|
| | Part A | |
| 1 | Dow Corning ® 345 (emollient) | 8.0 |
| 2 | Dow Corning ® 200 (emollient) | 2.0 |
| 3 | Dow Corning ® 5225 C (emulsifier) | 8.0 |
| | Part B | |
| 4 | AZG-442 (antiperspirant agent 35% solution) | 50.0 |
| 5 | Deionized (D.I.) Water | 12.0 |
| 6 | Butylene Glycol (humectant) | 8.0 |
| | Part C | |
| 7 | Deionized (D.I.) Water | 7.0 |
| 8 | Polymer of Ex. 8 (20 wt. % polymer solids) (gellant) | 5.0 |

EXAMPLE 19

An antiperspirant composition is formulated from the ingredients in Table 11.

TABLE 11

| | Ingredient | wt. % |
|---|---|---|
| | Part A | |
| 1 | Deionized (D.I.) Water | 17.4 |
| 2 | Disodium EDTA (chelating agent) | 0.2 |
| 3 | L.A.S. (emollient) | 3.0 |
| 4 | Butylene Glycol (humectant) | 5.0 |
| 5 | AZG-368 (antiperspirant agent 35% solution) | 43.0 |
| | Part B | |
| 6 | D.I. Water | 15.0 |
| 7 | Polymer of Ex. 8 (20 wt. % polymer solids) (gellant) | 12.0 |
| | Part C | |
| 8 | Denatured Ethanol (solvent) | 4.0 |
| | Part D | |
| 9 | Glydant Plus ® (preservative) | 0.4 |

The Part A ingredients are homogeneously mixed. The Part B ingredients are mixed in a separate container and added to Part B. The Part A+B components are homogeneously mixed. Part C and Part D are sequentially added with mixing to the Part A+B mixture to obtain the antiperspirant composition.

EXAMPLE 20

Antiperspirant compositions made according to Examples 14 and 19 are compared to commercially available clear antiperspirant gels for the presence of white residue following application to black Leneta paper. Comparisons are made to (A) Gillette® Series Antiperspirant & Deodorant ClearGel (Proctor & Gamble), (B) Old Spice® High Endurance Clear Gel Antiperspirant & Deodorant (Proctor & Gamble), and (C) Mitchum® For Women Clear Gel Antiperspirant & Deodorant (Revlon, Inc). The commercial antiperspirant product ingredients are listed in Table 12.

TABLE 12

| Commercial Antiperspirant | Active Ingredients | Inactive Ingredients | Initial Appearance |
|---|---|---|---|
| Gillette ® Series Antiperspirant & Deodorant ClearGel | Aluminum Zirconium Tetrachlorohydrex Gly (18.3%) | Water, Ethanol (denatured), Dimethicone, Propylene Glycol, Cyclomethicone, Dimethicone Copolyol, and Fragrance | Clear Gel |
| Old Spice ® High Endurance Clear Gel Antiperspirant & Deodorant | Aluminum Zirconium Tetrachlorohydrex Gly (19.2% anhydrous) | Water, Cyclopentasiloxane, Ethanol (denatured), Propylene Glycol, Dimethicone, Dimethicone Copolyol, and Fragrance | Clear Gel |
| Mitchum ® For Women Clear Gel Antiperspirant & Deodorant | Aluminum Zirconium Tetrachlorohydrex Gly (20%) | Water, Dipropylene Glycol, Cyclomethicone, Dimethicone, Glycerin, Dimethicone Copolyol, and Fragrance | Clear Gel |

Figure 2:
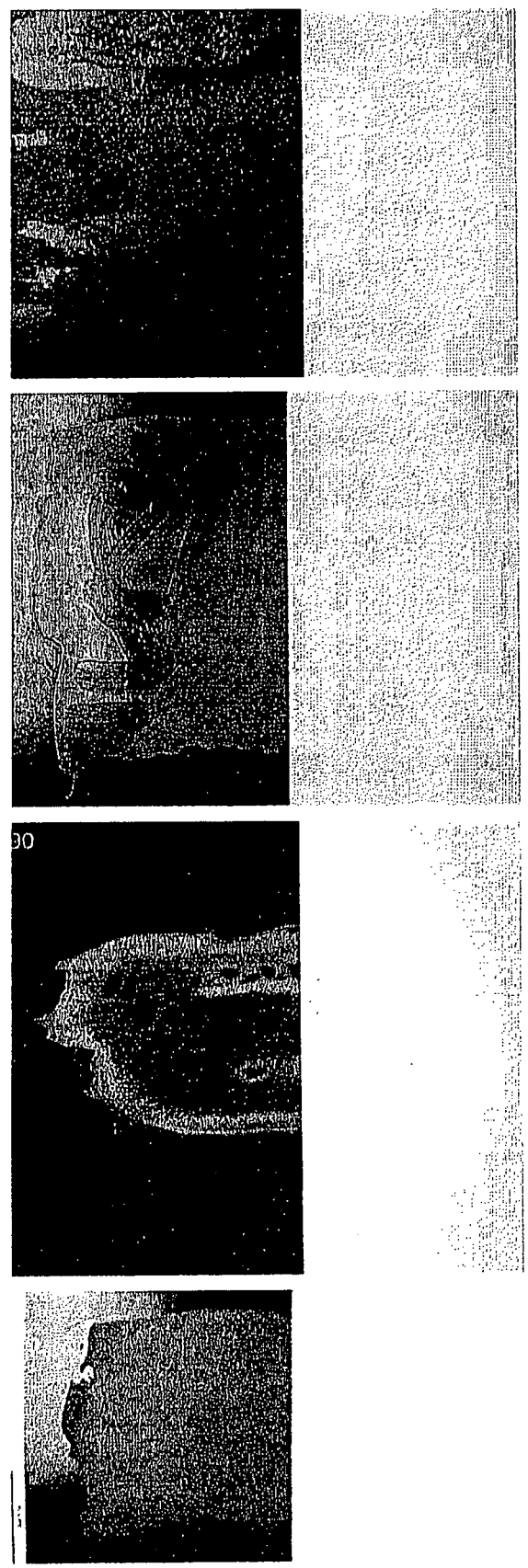
FIG. 2 shows side-by-side comparative photographs of dried commercially available antiperspirant films and the composition of Example 19. The films are drawn across Leneta opacity chart paper and evaluated for residual whitening.

One millimeter films of each antiperspirant composition are drawn across separate sheets of 194×260 mm Leneta Opacity Charts (Form 2C) in which the top half of the chart is black and the bottom half of the chart is white. The antiperspirant film is produced by pooling 5 to 10 grams of each sample onto the top of the opacity chart and drawing a BYK Gardner casting knife (calibrated to 1 mm wet thickness) across each pooled sample with a single downward stroke. The wet films of the experimental and commercial antiperspirants are clear. The films are dried at ambient room temperature for 24 hours at 50% RH. The opacity charts are visually observed for any visible white residue. Dried films of the antiperspirants of Examples 14 and 19 containing the cationic hydrophobically modified polymers of the invention exhibit no residual whitening whereas the dried films of all of the tested commercial antiperspirants show residual whitening. FIGS. 1 and 2 are representative of the superior results obtained with antiperspirants of the invention compared to the three commercial products tested.

EXAMPLE 21

Compositions made according to Example 18 were tested for white residue on skin. Comparisons were made with Gillette® Series Antiperspirant & Deodorant ClearGel set forth in Table 12 above. In a blind panel test, five panel subjects receive a controlled application of the respective antiperspirants on their forearms, and are asked to visually rate the products for the presence white residue after the films dry. Prior to application, a forearm of each panelist is washed with soap and water and patted dry. Two sites on the washed forearm are marked, one for the experimental sample and the other for the commercial product. The same quantities of antiperspirant (approximately 50 μL) are applied to the respective areas on the forearm and gently rubbed onto the surface of the skin. Care is taken not to overlap the test samples. Upon drying the panelists visually compare both test samples and are asked to identify the sample that leaves the least white residue. All five panelists rated the antiperspirant composition of Example 18 over the commercial product.

In one aspect, an exemplary embodiment of the invention relates to an antiperspirant composition comprising:
a) from about 0.5 wt. % to about 3 wt. % of a cationically hydrophobically modified polymer;
b) from about 72 wt. % to about 95 wt. % water; and
c) from about 5 wt. % to about 25 wt. % of an acidic antiperspirant agent.

In another aspect, an exemplary embodiment of the invention relates to an antiperspirant composition comprising:
a) from about 0.5 wt. % to about 3 wt. % of a cationically hydrophobically modified polymer;
b) from about 50 wt. % to about 95 wt. % water;
c) from about 5 wt. % to about 25 wt. % of an acidic antiperspirant agent; and
d) from about 0.1 wt. % to about 20 wt. % of a monoalcohol.

In another aspect of the invention an exemplary embodiment of the invention relates to an antiperspirant composition comprising:
a) from about 0.5 wt. % to about 3 wt. % of a cationically hydrophobically modified polymer;
b) from about 60 wt. % to about 95 wt. % water;
c) from about 5 wt. % to about 25 wt. % of an acidic antiperspirant agent; and
d) from about 0.1 wt % to about 10 wt. % of a polyhydric alcohol humectant.

In another aspect, an exemplary embodiment of the invention relates to an antiperspirant composition comprising:
a) from about 0.5 wt. % to about 2.5 wt. % of a cationically hydrophobically modified polymer;
b) from about 40 wt. % to about 95 wt. % water;
c) from about 5 wt. % to about 25 wt. % of an acidic antiperspirant agent;
d) from about 0.1 wt. % to about 20 wt. % of a monoalcohol; and
e) from about 0.1 wt. % to about 10 wt. % of polyhydric alcohol humectant.

In another aspect, an exemplary embodiment of the invention relates to an antiperspirant composition comprising:
a) from about 0.5 wt. % to about 3 wt. % of a cationically hydrophobically modified polymer;
b) from about 25 wt. % to about 90 wt. % water;
c) from about 5 wt. % to about 25 wt. % of an acidic antiperspirant agent;
d) from about 0.1 wt. % to about 20 wt. % of a silicone emulsifier;
e) from about 5 wt. % to about 30 wt. % of volatile silicone emollient; and
f) from about 0.1 wt. % to about 5 wt. % of an auxiliary gelling agent; all weights are based on the weight of the total antiperspirant composition.

The invention claimed is:
1. An antiperspirant composition comprising:
a) a cationically hydrophobically modified polymer;
b) water; and
c) an acidic antiperspirant agent wherein said cationically modified polymer comprises repeating units polymerized from a monomer mixture containing:
i) at least one amino-substituted vinyl monomer or salt thereof;
ii) at least one hydrophobic nonionic vinyl monomer;
iii) at least one associative vinyl monomer;
iv) at least one semihydrophobic vinyl surfactant monomer;
v) optionally, at least one hydroxy-substituted nonionic vinyl;
vi) optionally, a least one crosslinking monomer; and mixtures thereof; wherein said at least one associative vinyl monomer (iii) is selected from at least one monomer represented by formula (III):

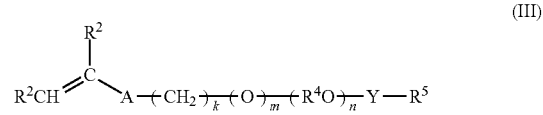

wherein, each $R^2$ is independently H, methyl, —C(O)OH, or —C(O)OR$^3$; $R^3$ is $C_1$-$C_{30}$ alkyl; A is —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0 and when k is in the range of 1 to about 30, m is 1; $(R^4-O)_n$ is a polyoxyalkylene, which is a homopolymer, a random copolymer, or a block copolymer of $C_2$-$C_4$ oxyalkylene units, wherein $R^4$ is $C_2H_4$, $C_3H_6$, $C_4H_8$, or a mixture thereof, and n is an integer in the range of about 5 to about 250; Y is —R$^4$O—, —R$^4$NH—, —C(O)—, —C(O)NH—, —R$^4$NHC(O)NH—, or —C(O)NHC(O)—; and $R^5$ is a substituted or unsubstituted alkyl selected from the group consisting of a $C_8$-$C_{40}$ linear alkyl, a $C_8$-$C_{40}$ branched alkyl, a $C_8$-$C_{40}$ carbocyclic alkyl, a $C_2$-$C_{40}$ alkyl-substituted phenyl, an aryl-substituted $C_2$-$C_{40}$ alkyl, and a $C_8$-$C_{80}$ complex ester; wherein the $R^5$ alkyl group optionally comprises one or more substituents selected from the group consisting of a hydroxyl group, an alkoxyl group, and a halogen group; and wherein said at least one semihydrophobic vinyl surfactant monomer (iv) is selected from at least one monomer represented by formulas (IV) or (V) and combinations thereof:

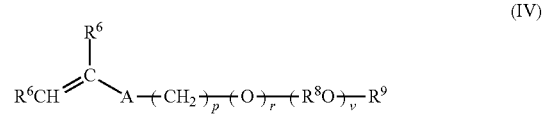

wherein, in each of formulas (IV) and (V), each $R^6$ is independently H, $C_1$-$C_{30}$ alkyl, —C(O)OH, or —C(O)OR$^7$; $R^7$ is $C_1$-$C_{30}$ alkyl; A is —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; p is an integer in the range of 0 to about 30, and r is 0 or 1, with the proviso that when p is 0, r is 0, and when p is in the range of 1 to about 30, r is 1; (R$^8$—O)$_v$ is a polyoxyalkylene, which is a homopolymer, a random copolymer or a block copolymer of C$_2$-C$_4$ oxyalkylene units, wherein R$^8$ is C$_2$H$_4$, C$_3$H$_6$, C$_4$H$_8$, or a mixture thereof, and v is an integer in the range of about 5 to about 250; R$^9$ is H or C$_1$-C$_4$ alkyl; and D is a C$_8$-C$_{30}$ unsaturated alkyl, or a carboxy-substituted C$_8$-C$_{30}$ unsaturated alkyl.

2. The composition of claim 1 wherein said amino-substituted vinyl monomer in said monomer mixture is selected from a mono-(C$_1$-C$_4$)alkylamino(C$_1$-C$_8$)alkyl (meth)acrylate, a di-(C$_1$-C$_4$)alkylamino(C$_1$-C$_8$)alkyl (meth)acrylate, a mono-(C$_1$-C$_4$)alkylamino(C$_1$-C$_8$)alkyl (meth)acrylamide, a di-(C$_1$-C$_4$)alkylamino(C$_1$-C$_8$)alkyl (meth)acrylamide, a nitrogen-containing heterocyclic (meth)acrylamide, a nitrogen-containing heterocyclic (meth)acrylate, and mixtures thereof.

3. The composition of claim 1 wherein said hydrophobic nonionic vinyl monomer in said monomer mixture is selected from at least one compound represented by the following formulas (I) or (II):

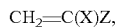  (I)

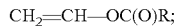  (II)

wherein, in each of formulas (I) and (II), X is H or methyl; and Z is —C(O)OR$^1$, —C(O)NH$_2$, —C(O)NHR$^1$, —C(O)N(R$^1$)$_2$, —C$_6$H$_4$R$^1$, —C$_6$H$_4$OR$^1$, —C$_6$H$_4$Cl , —CN, —NHC(O)CH$_3$, —NHC(O)H, N-(2-pyrrolidonyl), N-caprolactamyl, —C(O)NHC(CH$_3$)$_3$ ,—C(O)NHCH$_2$CH$_2$—N-ethyleneurea, —SiR$_3$, —C(O)O(CH$_2$)$_x$SiR$_3$, —C(O)NH(CH$_2$)$_x$SiR$_3$, or —(CH$_2$)$_x$SiR$_3$; x is an integer in the range of 1 to about 6; each R is independently C$_1$-C$_{30}$ alkyl; each R$^1$ is independently C$_1$-C$_{30}$ alkyl, hydroxy-substituted C$_2$-C$_{30}$ alkyl or halogen-substituted C$_1$-C$_{30}$ alkyl.

4. The composition of claim 1 wherein said hydrophobic nonionic vinyl monomer in said monomer mixture is a C$_1$-C$_{30}$ alkyl ester of acrylic acid, a C$_1$-C$_{30}$ alkyl ester of methacrylic acid, and mixtures thereof.

5. The composition of claim 1 wherein the associative vinyl monomer is selected from cetyl polyethoxylated methacrylate, cetearyl polyethoxylated methacrylate, stearyl polyethoxylated (meth)acrylate, arachidyl polyethoxylated (meth)acrylate, behenyl polyethoxylated methacrylate, lauryl polyethoxylated methacrylate, cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate, hydrogenated castor oil polyethoxylated methacrylate, canola polyethoxylated (meth)acrylate, and cholesterol polyethoxylated methacrylate, and a mixture thereof selected from cetyl polyethoxylated methacrylate, cetearyl polyethoxylated methacrylate, stearyl polyethoxylated (meth)acrylate, arachidyl polyethoxylated (meth)acrylate, behenyl polyethoxylated methacrylate, lauryl polyethoxylated methacrylate, cerotyl polyethoxylated (meth)acrylate, montanyl polyethoxylated (meth)acrylate, melissyl polyethoxylated (meth)acrylate, lacceryl polyethoxylated (meth) acrylate, tristyryl phenolpolyethoxylated methacrylate, hydrogenated castor oil polyethoxylated methacrylate, canola polyethoxylated (meth)acrylate, and cholesterol polyethoxylated methacrylate, and mixtures thereof.

6. The composition of claim 1 wherein said polyoxyalkylene moiety in said semihydrophobic vinyl surfactant monomer is a homopolymer, a random copolymer, or a block copolymer comprising about 5 to about 250 C$_2$-C$_4$ oxyalkylene units.

7. The composition of claim 1 wherein said semihydrophobic vinyl surfactant monomer is selected from a compound represented by at least one of formulas:

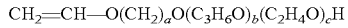

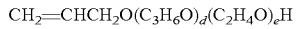

wherein a is 2, 3, or 4; b is an integer in the range of 1 to about 10; c is an integer in the range of about 5 to about 50; d is an integer in the range of 1 to about 10; and e is an integer in the range of about 5 to about 50.

8. The composition of claim 1 wherein said hydroxy-substituted nonionic vinyl monomer in said monomer mixture is selected from a hydroxy-substituted (C$_1$-C$_4$)alkyl acrylate, a hydroxy-substituted(C$_1$-C$_4$)alkyl methacrylate, hydroxy-substituted (C$_1$-C$_4$)alkyl acrylamide, a hydroxy-substituted (C$_1$-C$_4$)alkyl methacrylamide, and mixtures thereof.

9. The composition of claim 8 wherein said hydroxy-substituted nonionic vinyl monomer is 2-hydroxyethyl methacrylate.

10. The composition of claim 1 wherein said crosslinking monomer in said monomer mixture is selected from an acrylate ester of a polyol having at least two acrylate ester groups, a methacrylate ester of a polyol having at least two methacrylate ester groups, and mixtures thereof.

11. The composition of claim 1 wherein said acidic antiperspirant agent is selected from aluminum halides, aluminum hydroxyhalides, aluminum sulfate, zirconium (zirconyl) oxyhalides, zirconium (zirconyl) hydroxyhalides; complexes thereof; and mixtures thereof.

12. The composition of claim 11 wherein said acidic antiperspirant agent is selected from aluminum and zirconium salt complexes with an amino acid, a glycol, and mixtures thereof.

13. The composition of claim 1 wherein said acidic antiperspirant agent is selected from aluminum chloride, aluminum chlorohydrate, aluminum dichlorohydrate, aluminum sesquichlorohydrate, zirconyl hydroxychloride, aluminum chlorohydrex polyethylene glycol, aluminum chlorohydrex propylene glycol, aluminum dichlorohydrex polyethylene glycol, aluminum dichlorohydrex propylene glycol, aluminum sesquichlorohydrex polyethylene glycol, aluminum sesquichlorohydrex propylene glycol, aluminum zirconium trichlorohyrate, aluminum zirconium tetrachlorohyrate, aluminum zirconium pentachlorohyrate, aluminum zirconium octachlorohyrate, aluminum zirconium chlorohydrex glycine, aluminum zirconium trichlorohydrex glycine, aluminum zirconium tetrachlorohyrex glycine, aluminum zirconium pentachlorohyrex glycine, aaluminum zirconium octachlorohyrex glycine, ferric chloride, zirconium powder, and mixtures thereof.

14. The composition of claim 1 further comprising one or more components selected from auxiliary solvent(s)/drying agent(s) emollient(s), humectant(s), emulsifier(s), auxiliary gelling agent(s), auxiliary acidification agent(s), pH adjusting agent(s), preservative agent(s), deodorant agent(s), antimicrobial(s), chelating agent(s), botanical active(s), cosmetic bead(s), surfactant(s), suspending agent(s), antifoaming agent(s), film-former(s), skin protectant(s), binder(s), antifungal agent(s); absorbent(s); opacifying agent(s); pearlizing agent(s); colorants; pigment(s); antioxidant(s), propellant(s), spreading aid(s), physiologically active agent(s), astringent(s), vitamin(s), fragrance(s), fragrance solubilizers(s), titanium dioxide, calcium carbonate, talc, teatree powder, potato starch, tapioca starch, paraffin kaolin clay, zinc oxide, beeswax, zeolites, and silica.

15. The antiperspirant composition of claim 1 comprising:
   a) from about 0.5 wt. % to about 3 wt. % of said cationically hydrophobically modified polymer;
   b) from about 50 wt. % to about 95 wt. % water;
   c) from about 5 wt. % to about 25 wt. % of an acidic antiperspirant agent; and
   d) from about 0.1 wt. % to about 20 wt. % of a monoalcohol, wherein all weights are based on the weight of the total antiperspirant composition.

16. The composition of claim 15 further comprising:
   e) from about 0.1 wt. % to about 10 wt. % of polyhydric alcohol.

17. The composition of claim 1 comprising:
   a) from about 0.5 wt. % to about 3 wt. % of a cationically hydrophobically modified polymer;
   b) from about 25 wt. % to about 90 wt. % water;
   c) from about 5 wt. % to about 25 wt. % of an acidic antiperspirant agent;
   d) from about 0.1 wt. % to about 20 wt. % of a silicone emulsifier;
   e) from about 5 wt. % to about 30 wt. % of volatile silicone emollient; and
   f) from about 0.1 wt. % to about 5 wt. % of an auxiliary gelling agent; all weights are based on the weight of the total antiperspirant composition.

* * * * *